(12) United States Patent
Robin et al.

(10) Patent No.: US 9,603,708 B2
(45) Date of Patent: *Mar. 28, 2017

(54) LOW CROSSING PROFILE DELIVERY CATHETER FOR CARDIOVASCULAR PROSTHETIC IMPLANT

(75) Inventors: Kevin Robin, Rohnert Park, CA (US); Do Uong, Santa Rosa, CA (US); Gordon Bishop, Santa Rosa, CA (US)

(73) Assignee: DFM, LLC, Incline Village, NV (US)

( * ) Notice: Subject to any disclaimer, the term of this patent is extended or adjusted under 35 U.S.C. 154(b) by 218 days.

This patent is subject to a terminal disclaimer.

(21) Appl. No.: 13/110,780

(22) Filed: May 18, 2011

(65) Prior Publication Data
US 2012/0016468 A1    Jan. 19, 2012

Related U.S. Application Data

(60) Provisional application No. 61/346,390, filed on May 19, 2010, provisional application No. 61/411,862, filed on Nov. 9, 2010.

(51) Int. Cl.
*A61F 2/24* (2006.01)
*C08G 59/50* (2006.01)
(Continued)

(52) U.S. Cl.
CPC .......... *A61F 2/2418* (2013.01); *A61F 2/2436* (2013.01); *A61F 2/2439* (2013.01);
(Continued)

(58) Field of Classification Search
CPC .... A61F 2/2418; A61F 2/2436; A61F 2/2439; A61F 2/2412; A61F 2/24;
(Continued)

(56) References Cited

U.S. PATENT DOCUMENTS

| | | |
|---|---|---|
| 3,657,744 A | 4/1972 | Ersek |
| 3,671,979 A | 6/1972 | Moulopoulos |

(Continued)

FOREIGN PATENT DOCUMENTS

| | | |
|---|---|---|
| DE | 195 46 692 | 12/1995 |
| DE | 199 07 646 | 2/1999 |

(Continued)

OTHER PUBLICATIONS

International Search Report and Written Opinion, Appl. No. PCT/US2011/037201, mailed Feb. 9, 2012.
(Continued)

*Primary Examiner* — Alexander Orkin
(74) *Attorney, Agent, or Firm* — Knobbe, Martens, Olson & Bear, LLP.

(57) ABSTRACT

A delivery catheter and a method for deploying a cardiovascular prosthetic implant using a minimally invasive procedure are disclosed. The delivery catheter comprises an elongate, flexible catheter body having a proximal end and a distal end, wherein the distal end has an outer diameter of 18 French or less, a cardiovascular prosthetic implant at the distal end of the catheter body, wherein the cardiovascular prosthetic implant comprises an inflatable cuff and a tissue valve coupled to the inflatable cuff, and at least one link between the catheter body and the cardiovascular prosthetic implant.

22 Claims, 14 Drawing Sheets

(51) Int. Cl.
*C08L 63/00* (2006.01)
*A61M 25/06* (2006.01)

(52) U.S. Cl.
CPC .............. *C08G 59/50* (2013.01); *C08L 63/00* (2013.01); *A61F 2210/0085* (2013.01); *A61F 2220/005* (2013.01); *A61F 2220/0008* (2013.01); *A61F 2220/0016* (2013.01); *A61F 2220/0058* (2013.01); *A61F 2230/0078* (2013.01); *A61F 2250/0003* (2013.01); *A61M 2025/0681* (2013.01)

(58) Field of Classification Search
CPC ...... A61F 2210/0085; A61F 2230/0078; A61F 2250/0003
USPC ............................. 623/2.11, 2.12, 2.36–2.38
See application file for complete search history.

(56) References Cited

U.S. PATENT DOCUMENTS

| | | |
|---|---|---|
| 4,056,854 A | 11/1977 | Boretos et al. |
| 4,106,129 A | 8/1978 | Carpentier et al. |
| 4,183,102 A | 1/1980 | Guiset |
| 4,192,020 A | 3/1980 | Davis et al. |
| 4,213,207 A | 7/1980 | Wilson |
| 4,221,548 A | 9/1980 | Child |
| 4,316,503 A | 2/1982 | Kurachi et al. |
| 4,339,831 A | 7/1982 | Johnson |
| 4,592,340 A | 6/1986 | Boyles |
| 4,652,263 A | 3/1987 | Herweck et al. |
| 4,955,856 A | 9/1990 | Phillips |
| 4,994,077 A * | 2/1991 | Dobben .................. 623/2.2 |
| 5,119,148 A | 6/1992 | Anderson et al. |
| 5,149,150 A | 9/1992 | Davis |
| 5,167,628 A | 12/1992 | Boyles |
| 5,332,402 A | 7/1994 | Teitelbaum |
| 5,370,685 A | 12/1994 | Stevens |
| 5,370,691 A | 12/1994 | Samson |
| 5,397,351 A | 3/1995 | Pavcnik et al. |
| 5,411,552 A | 5/1995 | Andersen et al. |
| 5,423,851 A | 6/1995 | Samuels |
| 5,443,499 A | 8/1995 | Schmitt |
| 5,500,014 A | 3/1996 | Quijano et al. |
| 5,506,193 A | 4/1996 | Cederbaum et al. |
| 5,554,185 A | 9/1996 | Block et al. |
| 5,690,570 A | 11/1997 | Chang et al. |
| 5,697,968 A | 12/1997 | Rogers et al. |
| 5,871,537 A | 2/1999 | Bilge et al. |
| 5,957,949 A | 9/1999 | Leonhardt et al. |
| 5,980,570 A | 11/1999 | Simpson |
| 6,007,575 A | 12/1999 | Samuels |
| 6,027,525 A | 2/2000 | Suh et al. |
| 6,090,139 A | 7/2000 | Lemelson |
| 6,090,140 A | 7/2000 | Gabbay |
| 6,102,944 A | 8/2000 | Huynh et al. |
| 6,110,201 A | 8/2000 | Quijano et al. |
| 6,162,245 A | 12/2000 | Jayaraman |
| 6,165,215 A * | 12/2000 | Rottenberg et al. ......... 623/2.12 |
| 6,168,614 B1 | 1/2001 | Andersen et al. |
| 6,331,191 B1 | 12/2001 | Chobotov |
| 6,371,983 B1 | 4/2002 | Lane |
| 6,395,019 B2 | 5/2002 | Chobotov |
| 6,395,026 B1 | 5/2002 | Aboul-Hosn et al. |
| 6,409,759 B1 | 6/2002 | Peredo |
| 6,425,916 B1 | 7/2002 | Garrison et al. |
| 6,458,153 B1 | 10/2002 | Bailey et al. |
| 6,458,156 B1 | 10/2002 | Wan et al. |
| 6,471,723 B1 | 10/2002 | Ashworth et al. |
| 6,482,228 B1 | 11/2002 | Norred |
| 6,540,782 B1 | 4/2003 | Snyders |
| 6,582,462 B1 | 6/2003 | Andersen et al. |
| 6,602,280 B2 | 8/2003 | Chobotov |
| 6,776,604 B1 | 8/2004 | Chobotov et al. |
| 6,790,230 B2 | 9/2004 | Beyersdorf et al. |
| 6,835,188 B2 | 12/2004 | Samson et al. |
| 6,875,212 B2 | 4/2005 | Shaolian et al. |
| 6,896,690 B1 | 5/2005 | Lambrecht et al. |
| 6,945,957 B2 | 9/2005 | Freyman |
| 6,958,212 B1 | 10/2005 | Hubbell et al. |
| 6,989,027 B2 * | 1/2006 | Allen et al. ................. 623/2.18 |
| 7,066,951 B2 | 6/2006 | Chobotov |
| 7,090,693 B1 | 8/2006 | Chobotov et al. |
| 7,101,395 B2 * | 9/2006 | Tremulis et al. ............. 623/2.11 |
| 7,125,464 B2 | 10/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,178,978 B2 | 2/2007 | Argentine et al. |
| 7,192,441 B2 | 3/2007 | Sherry |
| 7,201,772 B2 | 4/2007 | Schwammenthal et al. |
| 7,276,078 B2 | 10/2007 | Bash et al. |
| 7,320,704 B2 | 1/2008 | Lashinski et al. |
| 7,329,279 B2 | 2/2008 | Haug et al. |
| 7,381,219 B2 | 6/2008 | Salahieh et al. |
| 7,429,269 B2 | 9/2008 | Schwammenthal et al. |
| 7,435,257 B2 | 10/2008 | Lashinski et al. |
| 7,442,204 B2 | 10/2008 | Schwammenthal et al. |
| 7,445,630 B2 | 11/2008 | Lashinski et al. |
| 7,445,631 B2 | 11/2008 | Salahieh et al. |
| 7,534,259 B2 | 5/2009 | Lashinski et al. |
| 7,534,261 B2 | 5/2009 | Friedman |
| 7,556,645 B2 * | 7/2009 | Lashinski et al. ............. 623/2.1 |
| 7,585,321 B2 | 9/2009 | Cribier |
| 7,628,805 B2 | 12/2009 | Bash et al. |
| 7,632,291 B2 | 12/2009 | Stephens et al. |
| 7,641,686 B2 | 1/2010 | Lashinski et al. |
| 7,658,762 B2 | 2/2010 | Lashinski et al. |
| 7,666,193 B2 | 2/2010 | Starksen et al. |
| 7,666,220 B2 | 2/2010 | Evans et al. |
| 7,678,217 B2 | 3/2010 | Chobotov et al. |
| 7,682,383 B2 | 3/2010 | Robin |
| 7,708,163 B2 | 5/2010 | Argentine |
| 7,712,606 B2 | 5/2010 | Salahieh et al. |
| 7,731,741 B2 | 6/2010 | Eidenschink |
| 7,744,912 B1 | 6/2010 | Hubbell et al. |
| 7,762,943 B2 | 7/2010 | Khairkhahan |
| 7,766,954 B2 | 8/2010 | Chobotov et al. |
| 7,780,726 B2 | 8/2010 | Seguin |
| 7,785,365 B2 | 8/2010 | Holman et al. |
| 7,799,068 B2 | 9/2010 | Holman et al. |
| 7,846,203 B2 | 12/2010 | Cribier |
| 7,935,144 B2 | 5/2011 | Robin et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,052,750 B2 | 11/2011 | Tuval et al. |
| 8,057,540 B2 | 11/2011 | Cribier et al. |
| 8,070,805 B2 | 12/2011 | Vidlund et al. |
| 8,092,525 B2 | 1/2012 | Eliasen et al. |
| 8,136,659 B2 | 3/2012 | Salahieh et al. |
| 8,137,398 B2 | 3/2012 | Tuval et al. |
| 8,142,497 B2 | 3/2012 | Friedman |
| 8,197,534 B2 | 6/2012 | Brumleve et al. |
| 8,308,796 B2 | 11/2012 | Lashinski et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,377,118 B2 | 2/2013 | Lashinski et al. |
| 8,414,643 B2 | 4/2013 | Tuval et al. |
| 8,454,656 B2 | 6/2013 | Tuval |
| 8,562,663 B2 | 10/2013 | Mearns et al. |
| 8,568,477 B2 | 10/2013 | Lashinski et al. |
| 8,584,849 B2 | 11/2013 | McCaffrey |
| 9,308,360 B2 | 4/2016 | Bishop et al. |
| 2001/0007956 A1 | 7/2001 | Letac et al. |
| 2001/0021872 A1 | 9/2001 | Bailey et al. |
| 2001/0044656 A1 | 11/2001 | Williamson, IV et al. |
| 2003/0004537 A1 | 1/2003 | Boyle et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0040772 A1 | 2/2003 | Hyodoh et al. |
| 2003/0055492 A1 * | 3/2003 | Shaolian et al. ............. 623/1.24 |

(56) References Cited

U.S. PATENT DOCUMENTS

| | | |
|---|---|---|
| 2003/0055496 A1* | 3/2003 | Cai et al. .................... 623/2.19 |
| 2003/0074045 A1 | 4/2003 | Buzzard et al. |
| 2003/0074058 A1 | 4/2003 | Sherry |
| 2003/0083741 A1* | 5/2003 | Woo et al. .................... 623/2.2 |
| 2003/0125793 A1 | 7/2003 | Vesely |
| 2003/0153974 A1 | 8/2003 | Spenser et al. |
| 2003/0220684 A1 | 11/2003 | Holman et al. |
| 2003/0236568 A1 | 12/2003 | Hojeibane et al. |
| 2004/0039436 A1 | 2/2004 | Spenser et al. |
| 2004/0210304 A1 | 10/2004 | Seguin et al. |
| 2004/0225354 A1 | 11/2004 | Allen et al. |
| 2004/0236411 A1* | 11/2004 | Sarac et al. .................... 623/1.26 |
| 2004/0260389 A1 | 12/2004 | Case et al. |
| 2004/0260390 A1 | 12/2004 | Sarac et al. |
| 2005/0090804 A1 | 4/2005 | Chobotov et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137692 A1 | 6/2005 | Haug et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1* | 6/2005 | Salahieh et al. ............ 623/2.38 |
| 2005/0143809 A1 | 6/2005 | Salahieh et al. |
| 2005/0158272 A1 | 7/2005 | Whirley et al. |
| 2005/0171593 A1 | 8/2005 | Whirley et al. |
| 2005/0203614 A1 | 9/2005 | Forster et al. |
| 2005/0209687 A1 | 9/2005 | Sitzmann et al. |
| 2005/0251251 A1 | 11/2005 | Cribier |
| 2005/0283231 A1 | 12/2005 | Haug et al. |
| 2006/0004442 A1 | 1/2006 | Spenser et al. |
| 2006/0020332 A1* | 1/2006 | Lashinski et al. ........... 623/2.11 |
| 2006/0020334 A1 | 1/2006 | Lashinski et al. |
| 2006/0058872 A1 | 3/2006 | Salahieh et al. |
| 2006/0088836 A1 | 4/2006 | Wohlgemuth et al. |
| 2006/0149360 A1 | 7/2006 | Schwammenthal et al. |
| 2006/0173524 A1 | 8/2006 | Salahieh et al. |
| 2006/0178732 A1 | 8/2006 | Chobotov et al. |
| 2006/0195183 A1* | 8/2006 | Navia et al. .................... 623/2.18 |
| 2006/0206193 A1 | 9/2006 | Chobotov et al. |
| 2006/0217637 A1 | 9/2006 | Leiboff et al. |
| 2006/0222596 A1 | 10/2006 | Askari et al. |
| 2006/0224232 A1 | 10/2006 | Chobotov |
| 2006/0235512 A1* | 10/2006 | Osborne et al. ............ 623/2.17 |
| 2006/0253191 A1 | 11/2006 | Salahieh et al. |
| 2006/0259134 A1 | 11/2006 | Schwammenthal et al. |
| 2006/0271172 A1 | 11/2006 | Tehrani |
| 2007/0010877 A1 | 1/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0219630 A1* | 9/2007 | Chu ............................ 623/2.11 |
| 2007/0244552 A1 | 10/2007 | Salahieh et al. |
| 2007/0270932 A1 | 11/2007 | Headley et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0125859 A1 | 5/2008 | Salahieh et al. |
| 2008/0200980 A1 | 8/2008 | Robin et al. |
| 2008/0234814 A1 | 9/2008 | Salahieh et al. |
| 2008/0243081 A1 | 10/2008 | Nance et al. |
| 2009/0054969 A1 | 2/2009 | Salahieh et al. |
| 2009/0054976 A1 | 2/2009 | Tuval et al. |
| 2009/0076598 A1 | 3/2009 | Salahieh et al. |
| 2009/0088836 A1 | 4/2009 | Bishop et al. |
| 2009/0099649 A1 | 4/2009 | Chobotov et al. |
| 2009/0234443 A1 | 9/2009 | Ottma et al. |
| 2009/0264984 A1 | 10/2009 | Chobotov |
| 2009/0264997 A1 | 10/2009 | Salahieh et al. |
| 2010/0004728 A1 | 1/2010 | Rao et al. |
| 2010/0004730 A1 | 1/2010 | Benjamin et al. |
| 2010/0010623 A1 | 1/2010 | Lashinski et al. |
| 2010/0016942 A1 | 1/2010 | Chobotov et al. |
| 2010/0016943 A1 | 1/2010 | Chobotov |
| 2010/0016948 A1 | 1/2010 | Chobotov |
| 2010/0030327 A1 | 2/2010 | Chatel |
| 2010/0048987 A1 | 2/2010 | Khairkhahan |
| 2010/0076481 A1 | 3/2010 | Stephens et al. |
| 2010/0106087 A1 | 4/2010 | Evans et al. |
| 2010/0121434 A1 | 5/2010 | Paul et al. |
| 2010/0132892 A1 | 6/2010 | Chobotov et al. |
| 2010/0168844 A1 | 7/2010 | Bergheim |
| 2010/0185275 A1* | 7/2010 | Richter et al. ............... 623/2.11 |
| 2010/0234852 A1 | 9/2010 | Shinohara et al. |
| 2010/0256754 A1 | 10/2010 | Styrc |
| 2010/0292772 A1 | 11/2010 | Samuels |
| 2010/0324668 A1 | 12/2010 | Maurer et al. |
| 2011/0060407 A1 | 3/2011 | Ketai et al. |
| 2011/0066170 A1 | 3/2011 | Farnan |
| 2011/0066233 A1 | 3/2011 | Thornton et al. |
| 2011/0098802 A1 | 4/2011 | Braido et al. |
| 2011/0112625 A1 | 5/2011 | Ben-Muvhar et al. |
| 2011/0153009 A1 | 6/2011 | Navia et al. |
| 2011/0160846 A1 | 6/2011 | Bishop et al. |
| 2011/0213460 A1 | 9/2011 | Lashinski et al. |
| 2011/0257733 A1 | 10/2011 | Dwork |
| 2011/0295354 A1 | 12/2011 | Bueche et al. |
| 2012/0016468 A1 | 1/2012 | Robin et al. |
| 2012/0022629 A1 | 1/2012 | Perera et al. |
| 2012/0078237 A1 | 3/2012 | Wang et al. |
| 2012/0226341 A1 | 9/2012 | Schreck et al. |
| 2012/0277855 A1 | 11/2012 | Lashinski et al. |
| 2013/0041458 A1 | 2/2013 | Lashinski et al. |
| 2013/0297010 A1 | 11/2013 | Bishop et al. |
| 2013/0297011 A1 | 11/2013 | Morris et al. |
| 2014/0163667 A1 | 6/2014 | Lashinski et al. |
| 2015/0094795 A1 | 4/2015 | Ginn et al. |
| 2016/0045311 A1 | 2/2016 | McCann et al. |
| 2016/0100963 A1 | 4/2016 | Aristizabal et al. |

FOREIGN PATENT DOCUMENTS

| | | |
|---|---|---|
| EP | 0 275 535 | 7/1988 |
| EP | 2241284 A1 | 10/2010 |
| JP | 59-005299 | 2/1984 |
| JP | 61-003499 | 2/1986 |
| JP | 10-507097 | 7/1998 |
| JP | 2000-513248 | 10/2000 |
| JP | 2002-535037 | 10/2002 |
| JP | 2003-505146 | 2/2003 |
| JP | 2004-502499 | 1/2004 |
| JP | 2005-515836 | 6/2005 |
| JP | 2007-536003 | 12/2007 |
| JP | 2008-541997 | 11/2008 |
| WO | WO 91/17720 | 11/1991 |
| WO | WO 93/01768 | 2/1993 |
| WO | WO 96/02212 | 2/1996 |
| WO | WO 97/30659 | 8/1997 |
| WO | WO 97/46177 | 11/1997 |
| WO | WO 98/43556 | 10/1998 |
| WO | WO 99/39662 | 8/1999 |
| WO | WO 00/41652 | 7/2000 |
| WO | WO 00/42950 | 7/2000 |
| WO | WO 00/47139 | 8/2000 |
| WO | WO 00/51522 | 9/2000 |
| WO | WO 01/06959 | 2/2001 |
| WO | WO 01/49213 | 7/2001 |
| WO | WO 01/62189 | 8/2001 |
| WO | WO 01/64137 | 9/2001 |
| WO | WO 03/003949 | 1/2003 |
| WO | WO 03/011195 | 2/2003 |
| WO | WO 03/047468 | 6/2003 |
| WO | WO 03/053288 | 7/2003 |
| WO | WO 03/053289 | 7/2003 |
| WO | WO 03/094799 | 11/2003 |
| WO | WO 03/096932 | 11/2003 |
| WO | WO 2005/107650 | 11/2005 |
| WO | WO 2006/116725 | 11/2006 |
| WO | WO 2006/127756 | 11/2006 |

(56) References Cited

FOREIGN PATENT DOCUMENTS

| | | |
|---|---|---|
| WO | WO 2006/133294 | 12/2006 |
| WO | WO 2010/117367 | 10/2010 |
| WO | WO 2011/033427 | 3/2011 |
| WO | WO 2011/035154 | 3/2011 |
| WO | WO 2011/105979 | 9/2011 |
| WO | WO 2011/146745 | 11/2011 |
| WO | WO 2012/023980 | 2/2012 |
| WO | WO 2012/023981 | 2/2012 |
| WO | WO 2012/024428 | 2/2012 |
| WO | WO 2013/165896 | 11/2013 |

OTHER PUBLICATIONS

International Preliminary Report on Patentability in PCT Application No. PCT/US2011/037201 dated Nov. 29, 2012.
Carabello, Blase, "Timing of Valve Replacement in Aortic Stenosis Moving Closer to Perfection," Circulation, 1997, vol. 95, pp. 2241-2243.

* cited by examiner

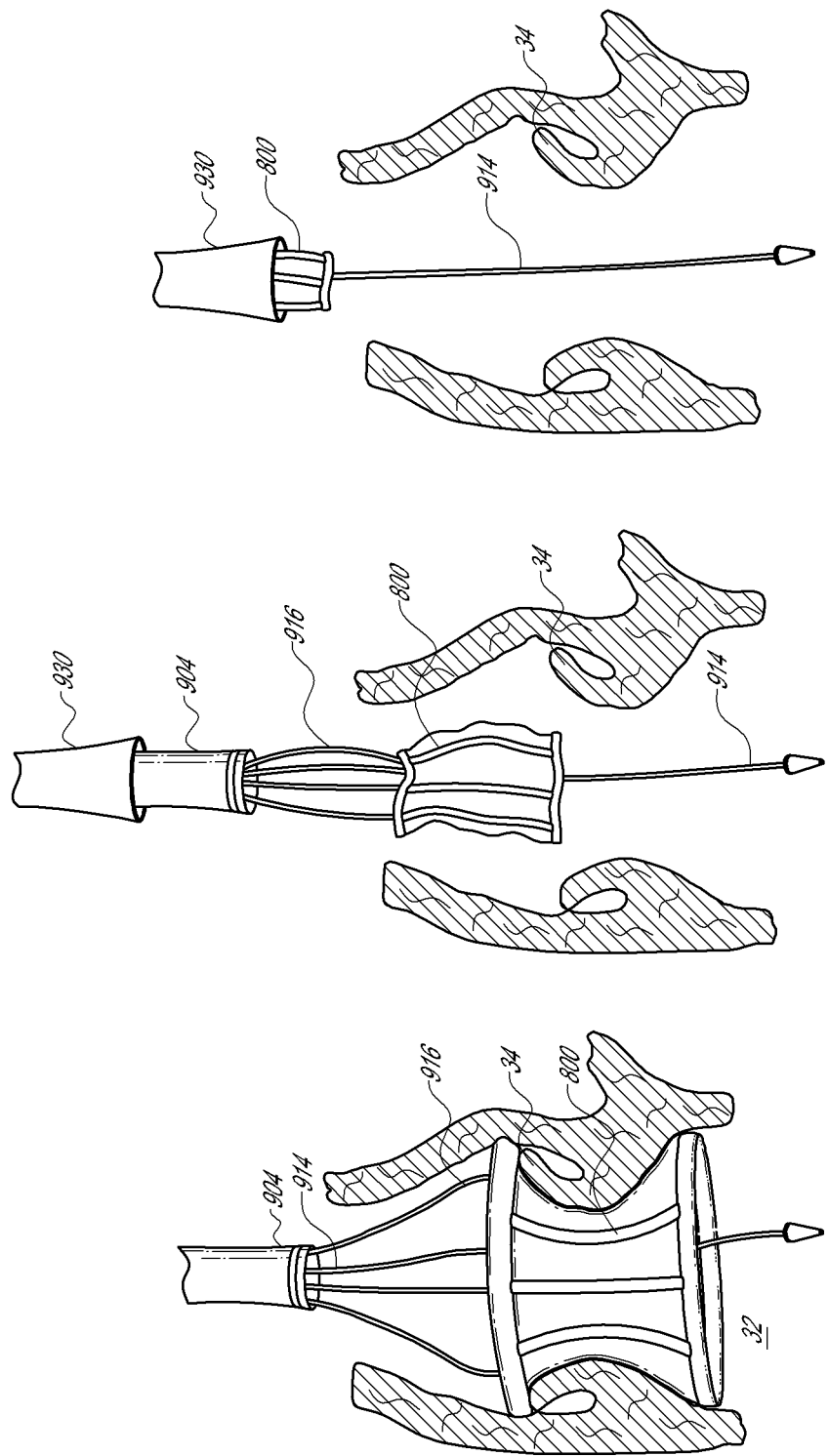

LOW CROSSING PROFILE DELIVERY CATHETER FOR CARDIOVASCULAR PROSTHETIC IMPLANT

CROSS-REFERENCE TO RELATED APPLICATIONS

This application claims the priority benefit to U.S. Provisional No. 61/346,390 filed May 19, 2010 and U.S. Provisional No. 61/411,862 filed Nov. 9, 2010, the entireties of which are hereby incorporated by reference herein.

BACKGROUND OF THE INVENTION

Field of the Invention

The present invention relates to medical methods and devices, and, in particular, to a low crossing profile delivery catheter for percutaneously implanting a cardiovascular implant having a formed-in-place support structure.

Description of the Related Art

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

The circulatory system is a closed loop bed of arterial and venous vessels supplying oxygen and nutrients to the body extremities through capillary beds. The driver of the system is the heart providing correct pressures to the circulatory system and regulating flow volumes as the body demands. Deoxygenated blood enters heart first through the right atrium and is allowed to the right ventricle through the tricuspid valve. Once in the right ventricle, the heart delivers this blood through the pulmonary valve and to the lungs for a gaseous exchange of oxygen. The circulatory pressures carry this blood back to the heart via the pulmonary veins and into the left atrium. Filling of the left atrium occurs as the mitral valve opens allowing blood to be drawn into the left ventricle for expulsion through the aortic valve and on to the body extremities. When the heart fails to continuously produce normal flow and pressures, a disease commonly referred to as heart failure occurs.

Heart failure simply defined is the inability for the heart to produce output sufficient to demand. Mechanical complications of heart failure include free-wall rupture, septal-rupture, papillary rupture or dysfunction aortic insufficiency and tamponade. Mitral, aortic or pulmonary valve disorders lead to a host of other conditions and complications exacerbating heart failure further. Other disorders include coronary disease, hypertension, and a diverse group of muscle diseases referred to as cardiomyopothies. Because of this syndrome establishes a number of cycles, heart failure begets more heart failure.

Heart failure as defined by the New York Heart Association in a functional classification.

I. Patients with cardiac disease but without resulting limitations of physical activity. Ordinary physical activity does not cause undue fatigue, palpitation, dyspnea, or anginal pain.

II. Patient with cardiac disease resulting in slight limitation of physical activity. These patients are comfortable at rest. Ordinary physical activity results in fatigue, palpitation, dyspnea, or anginal pain.

III. Patients with cardiac disease resulting in marked limitation of physical activity. These patients are comfortable at rest. Less than ordinary physical activity causes fatigue palpitation, dyspnea, or anginal pain.

IV. Patients with cardiac disease resulting in inability to carry on any physical activity without discomfort. Symptoms of cardiac insufficiency or of the anginal syndrome may be present even at rest. If any physical activity is undertaken, discomfort is increased.

There are many styles of mechanical valves that utilize both polymer and metallic materials. These include single leaflet, double leaflet, ball and cage style, slit-type and emulated polymer tricuspid valves. Though many forms of valves exist, the function of the valve is to control flow through a conduit or chamber. Each style will be best suited to the application or location in the body it was designed for.

Bioprosthetic heart valves comprise valve leaflets formed of flexible biological material. Bioprosthetic valves or components from human donors are referred to as homografts and xenografts are from non-human animal donors. These valves as a group are known as tissue valves. This tissue may include donor valve leaflets or other biological materials such as bovine pericardium. The leaflets are sewn into place and to each other to create a new valve structure. This structure may be attached to a second structure such as a stent or cage or other prosthesis for implantation to the body conduit.

Implantation of valves into the body has been accomplished by a surgical procedure and has been attempted via percutaneous method such as a catheterization or delivery mechanism utilizing the vasculature pathways. Surgical implantation of valves to replace or repair existing valves structures include the four major heart valves (tricuspid, pulmonary, mitral, aortic) and some venous valves in the lower extremities for the treatment of chronic venous insufficiency. Implantation includes the sewing of a new valve to the existing tissue structure for securement. Access to these sites generally include a thoracotomy or a sternotomy for the patient and include a great deal of recovery time. An open-heart procedure can include placing the patient on heart bypass to continue blood flow to vital organs such as the brain during the surgery. The bypass pump will continue to oxygenate and pump blood to the body's extremities while the heart is stopped and the valve is replaced. The valve may replace in whole or repair defects in the patient's current native valve. The device may be implanted in a conduit or other structure such as the heart proper or supporting tissue surrounding the heart. Attachments methods may include suturing, hooks or barbs, interference mechanical methods or an adhesion median between the implant and tissue.

Although valve repair and replacement can successfully treat many patients with valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Since surgical techniques are highly invasive and in the instance of a heart valve, the patient must be put on bypass during the operation, the need for a less invasive method of heart valve replacement has long been recognized. At least as early as 1972, the basic concept of suturing a tissue aortic valve to an expandable cylindrical "fixation sleeve" or stent was disclosed. See U.S. Pat. No. 3,657,744 to Ersek. Other early efforts were disclosed in U.S. Pat. No. 3,671,979 to Moulopoulos and U.S. Pat. No. 4,056,854 to Boretos, relating to prosthetic valves carried by an expandable valve support delivered via catheter for remote placement. More recent iterations of the same basic concept were disclosed, for example, in patents such as U.S. Pat. Nos. 5,411,552, 5,957,949, 6,168,614, and 6,582,462 to Anderson, et al., which relate generally to tissue valves carried by expandable metallic stent support structures which are crimped to a delivery balloon for later expansion at the implantation site.

In each of the foregoing systems, the tissue or artificial valve is first attached to a preassembled, complete support structure (some form of a stent) and then translumenally advanced along with the support structure to an implantation site. The support structure is then forceably enlarged or allowed to self expand without any change in its rigidity or composition, thereby securing the valve at the site.

Despite the many years of effort, and enormous investment of entrepreneurial talent and money, no stent based heart valve system has yet received regulatory approval, and a variety of difficulties remain. For example, stent based systems have a fixed rigidity even in the collapsed configuration, and have inherent difficulties relating to partial deployment, temporary deployment, removal and navigation.

Thus, a need remains for improvements over the basic concept of a stent based prosthetic valve. As disclosed herein a variety of significant advantages may be achieved by eliminating the stent and advancing the valve to the site without a support structure. Only later, the support structure is created in situ such as by inflating one or more inflatable chambers to impart rigidity to an otherwise highly flexible and functionless subcomponent.

SUMMARY OF THE INVENTION

One aspect of the present invention comprises a delivery catheter for deploying a cardiovascular prosthetic implant using a minimally invasive procedure. The delivery catheter comprises an elongate, flexible catheter body having a proximal end and a distal end. The distal portion of the catheter has an outer diameter of 18 French or less. A cardiovascular prosthetic implant is positioned at the distal end of the catheter body. The cardiovascular prosthetic implant comprises an inflatable cuff and a tissue valve having a thickness of at least about 0.011 inches coupled to the inflatable cuff. At least one link is provided between the catheter body and the cardiovascular prosthetic implant Another aspect of the present invention comprises a method of deploying a cardiovascular prosthetic implant. The method includes translumenally advancing a catheter having a distal portion with a diameter of 18 French and carrying a cardiovascular prosthetic implant with a tissue valve having a thickness of at least about 0.011 inches to a position proximate a native valve of a patient. The cardiovascular prosthetic implant comprises an inflatable cuff, a tissue valve coupled to the inflatable cuff. The inflatable cuff is inflated fully with a hardenable inflation media. The catheter is removed from the patient, leaving the hardenable inflation media in the cardiovascular prosthetic implant within the patient.

Another aspect of the present invention comprises a delivery catheter for deploying a cardiovascular prosthetic implant using a minimally invasive procedure. The delivery catheter comprises an elongate, flexible catheter body having a proximal end and a distal end, wherein the distal end has an outer diameter of 18 French or less. A cardiovascular prosthetic implant is positioned at the distal end of the catheter body. The cardiovascular prosthetic implant comprises a support structure and a tissue valve having a thickness of at least about 0.011 inches coupled to the support structure Another aspect of the present invention comprises a method of deploying a cardiovascular prosthetic implant. The method comprises translumenally advancing a catheter having a distal portion with a diameter of 18 French and carrying a cardiovascular prosthetic implant with a tissue valve having a thickness of at least about 0.011 inches to a position proximate a native valve of a patient. The cardiovascular prosthetic implant is deployed within the patient and the catheter is removed from the patient.

BRIEF DESCRIPTION OF THE DRAWINGS

FIGS. 10A-C illustrates time sequence steps of deploying and withdrawing an artificial valve implant.

DETAILED DESCRIPTION OF THE EMBODIMENTS

Figure 1:
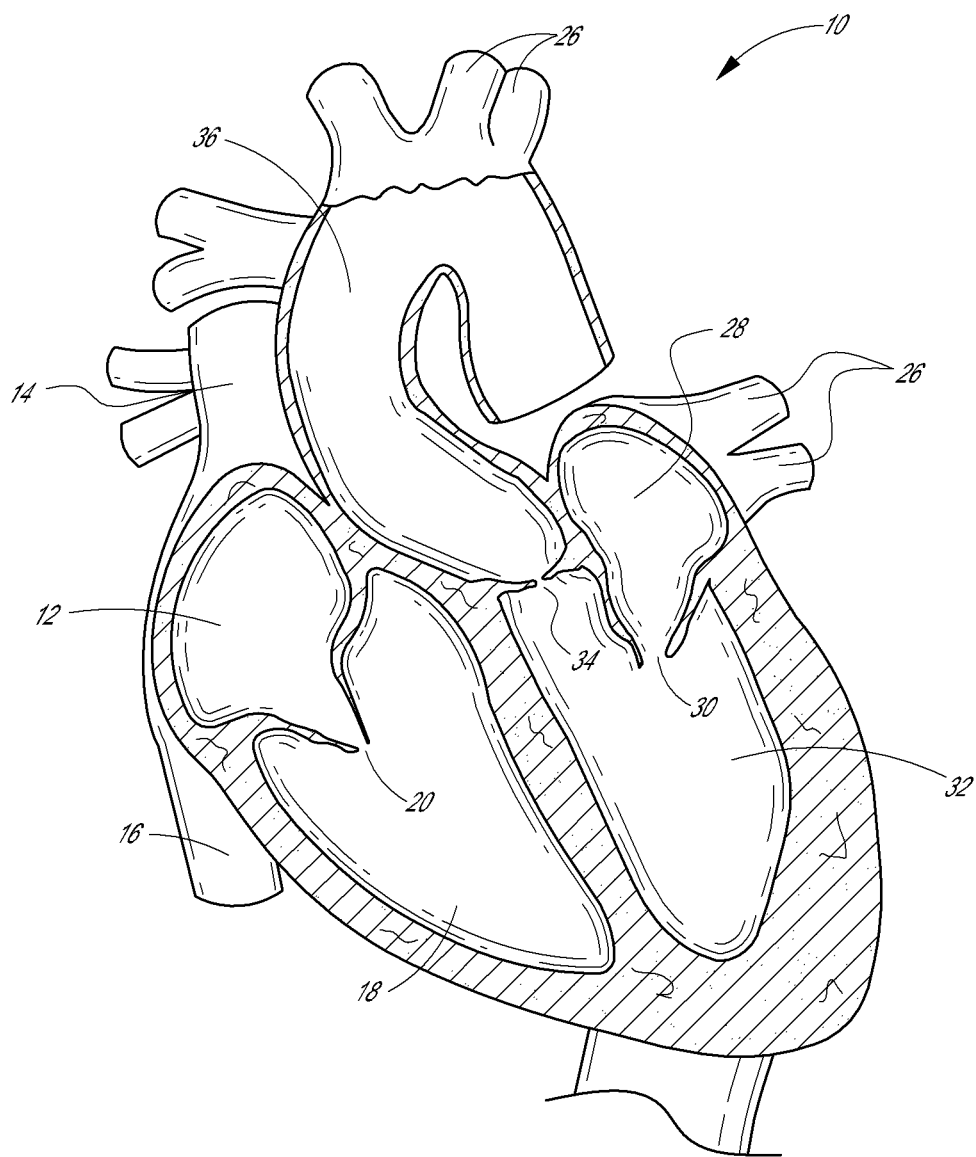
FIG. 1 is a cross-sectional schematic view of a heart and its major blood vessels.

FIG. 1 is a schematic cross-sectional illustration of the anatomical structure and major blood vessels of a heart 10. Deoxygenated blood is delivered to the right atrium 12 of the heart 10 by the superior and inferior vena cava 14, 16. Blood in the right atrium 12 is allowed into the right ventricle 18 through the tricuspid valve 20. Once in the right ventricle 18, the heart 10 delivers this blood through the pulmonary valve 22 to the pulmonary arteries 24 and to the lungs for a gaseous exchange of oxygen. The circulatory pressures carry this blood back to the heart via the pulmonary veins 26 and into the left atrium 28. Filling of the left atrium 28 occurs as the mitral valve 30 opens allowing blood to be drawn into the left ventricle 32 for expulsion through the aortic valve 34 and on to the body extremities through the aorta 36. When the heart 10 fails to continuously produce normal flow and pressures, a disease commonly referred to as heart failure occurs.

One cause of heart failure is failure or malfunction of one or more of the valves of the heart 10. For example, the aortic valve 34 can malfunction for several reasons. For example, the aortic valve 34 may be abnormal from birth (e.g., bicuspid, calcification, congenital aortic valve disease), or it could become diseased with age (e.g., acquired aortic valve disease). In such situations, it can be desirable to replace the abnormal or diseased valve 34.

FIG. 2 is a schematic illustration of the left ventricle 32, which delivers blood to the aorta 36 through the aortic valve 34. The aorta 36 comprises (i) the ascending aorta 38, which arises from the left ventricle 32 of the heart 10, (ii) the aortic arch 10, which arches from the ascending aorta 38 and (iii) the descending aorta 42 which descends from the aortic arch 40 towards the abdominal aorta (not shown). Also shown are the principal branches of the aorta 14, which include the innomate artery 44 that immediately divides into the right carotid artery (not shown) and the right subclavian artery (not shown), the left carotid 46 and the subclavian artery 48.

Inflatable Prosthetic Aortic Valve Implant

Figure 2A:
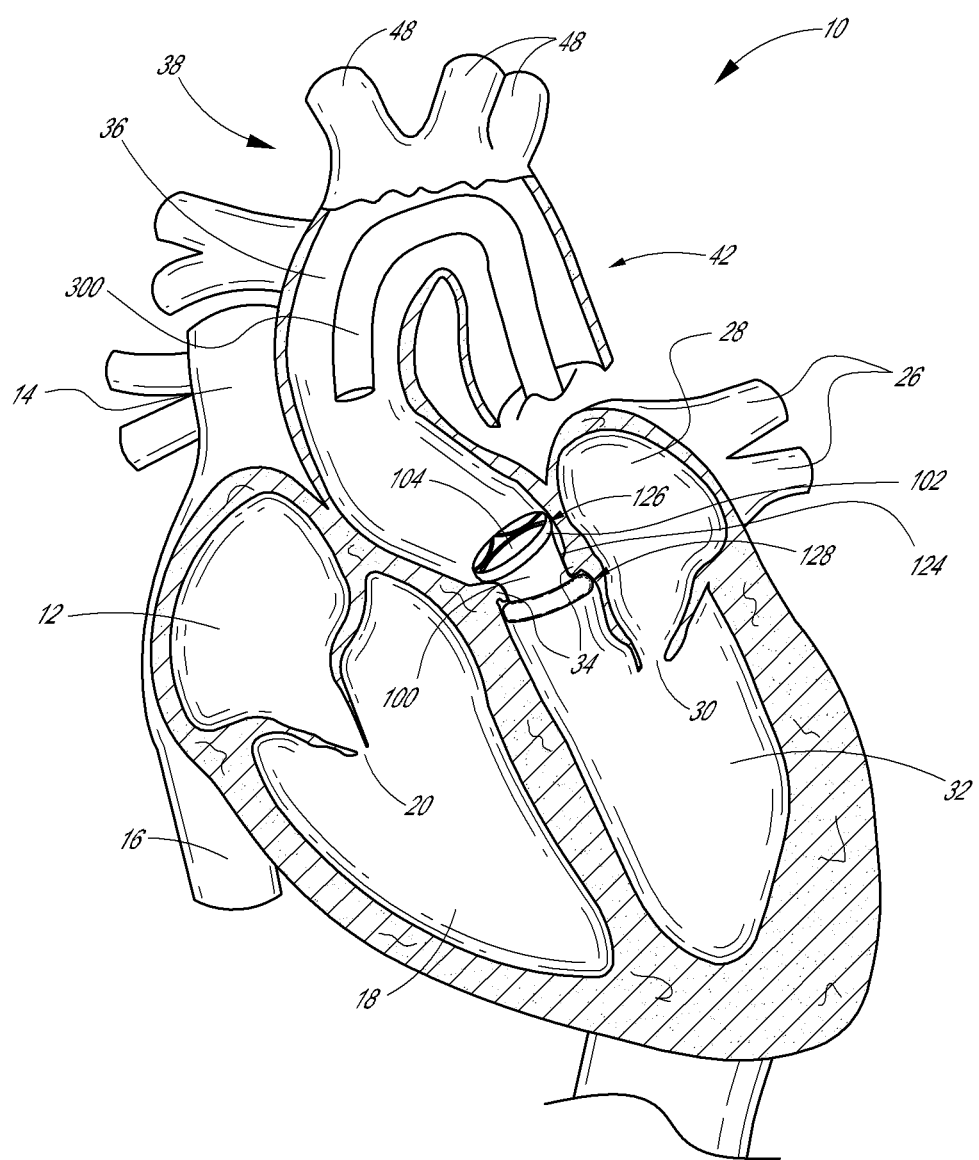
FIG. 2A is a partial cut-away view a left ventricle and aortic with an prosthetic aortic valve implant according to one embodiment of the present invention positioned therein.

With continued reference to FIG. 2A, a cardiovascular prosthetic implant 800 in accordance with an embodiment of the present invention is shown spanning the native abnormal or diseased aortic valve 34. The implant 800 and various modified embodiments thereof will be described in detail below. As will be explained in more detail below, the implant 800 is preferably delivered minimally invasively using an intravascular delivery catheter 900 or trans apical approach with a trocar.

In the description below, the present invention will be described primarily in the context of replacing or repairing an abnormal or diseased aortic valve 34. However, various features and aspects of methods and structures disclosed herein are applicable to replacing or repairing the mitral 30, pulmonary 22 and/or tricuspid 20 valves of the heart 10 as those of skill in the art will appreciate in light of the disclosure herein. In addition, those of skill in the art will also recognize that various features and aspects of the methods and structures disclosed herein can be used in other parts of the body that include valves or can benefit from the addition of a valve, such as, for example, the esophagus, stomach, ureter and/or vesice, biliary ducts, the lymphatic system and in the intestines.

In addition, various components of the implant and its delivery system will be described with reference to coordinate system comprising "distal" and "proximal" directions. In this application, distal and proximal directions refer to the deployment system 900, which is used to deliver the implant 800 and advanced through the aorta 36 in a direction opposite to the normal direction of blood through the aorta 36. Thus, in general, distal means closer to the heart while proximal means further from the heart with respect to the circulatory system.

Figure 2B:
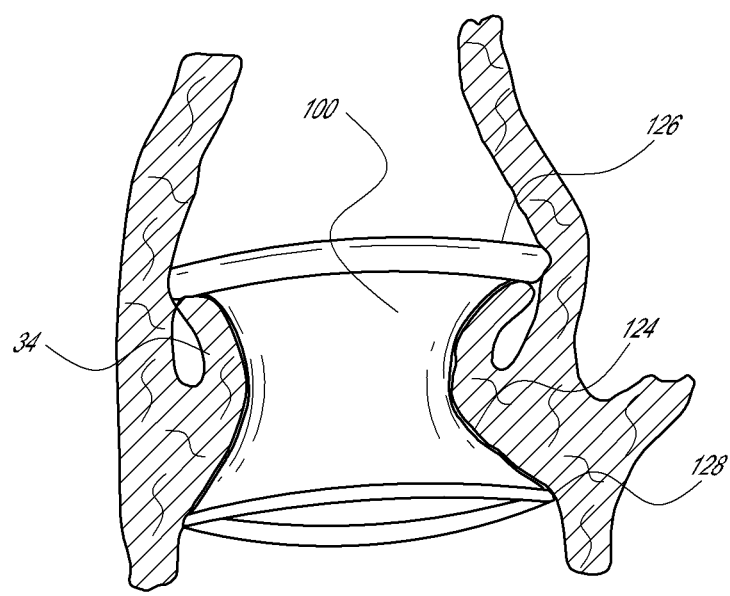
FIG. 2B is a side view of the implant of FIG. 2A positioned across a native aortic valve.

In some embodiments, the implant 800 may be a prosthetic aortic valve implant. With reference to FIG. 2B in the illustrated embodiment, the implant 800 has a shape that can be viewed as a tubular member or hyperboloid shape where a waist 805 excludes the native valve 34 or vessel and proximally the proximal end 803 forms a hoop or ring to seal blood flow from re-entering the left ventricle 32. Distally, the distal end 804 also forms a hoop or ring to seal blood from forward flow through the outflow track. Between the two ends 803 and 804, the valve 104 is mounted to the cuff or body 802 such that when inflated the implant 800 excludes the native valve 34 or extends over the former location of the native valve 34 and replaces its function. The distal end 804 should have an appropriate size and shape so that it does not interfere with the proper function of the mitral valve, but still secures the valve adequately. For example, there may be a notch, recess or cut out in the distal end 804 of the device to prevent mitral valve interference. The proximal end 803 is designed to sit in the aortic root. It is preferably shaped in such a way that it maintains good apposition with the wall of the aortic root. This prevents the device from migrating back into the ventricle 32. In some embodiments, the implant 800 is configured such that it does not extend so high that it interferes with the coronary arteries.

Any number of additional inflatable rings or struts may be disposed between the proximal end 803 and distal end 804. The distal end 804 of the implant 800 is preferably positioned within the left ventricle 34 and can utilize the aortic root for axial stabilization as it may have a larger diameter than the aortic lumen. This may lessen the need for hooks, barbs or an interference fit to the vessel wall. Since the implant 800 may be placed without the aid of a dilatation balloon for radial expansion, the aortic valve 34 and vessel may not have any duration of obstruction and would provide the patient with more comfort and the physician more time to properly place the device accurately. Since the implant 800 is not utilizing a support member with a single placement option as a plastically deformable or shaped memory metal stent does, the implant 800 may be movable and or removable if desired. This could be performed multiple times until the implant 800 is permanently disconnected from the delivery catheter 900 as will be explained in more detail below. In addition, the implant 800 can include features, which allow the implant 800 to be tested for proper function, sealing and sizing, before the catheter 900 is disconnected.

Figure 3A:
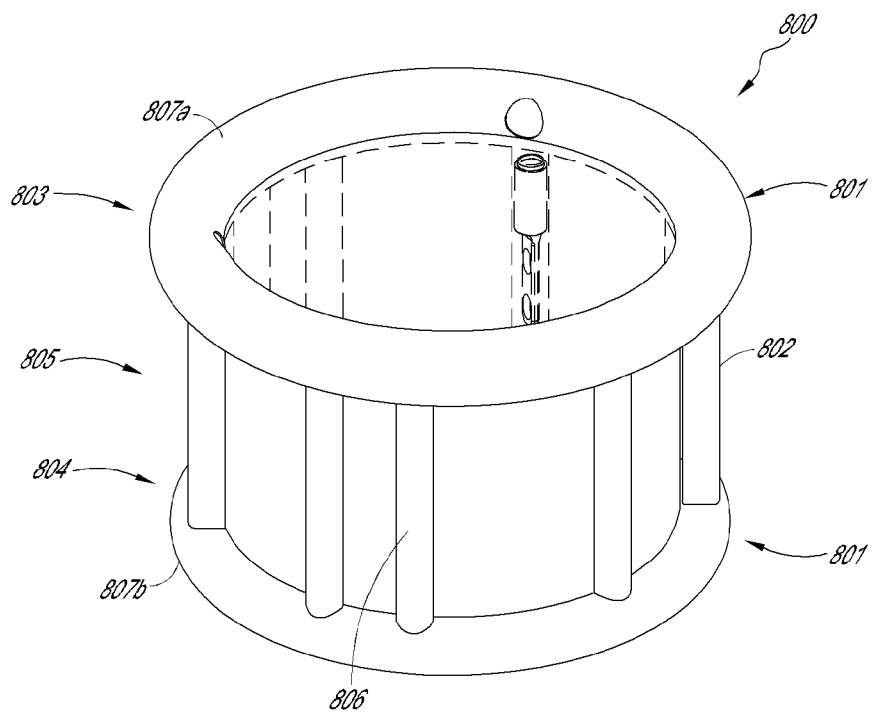
FIG. 3A is a front perspective view of the implant of FIG. 2B.

With reference to FIG. 3A, the implant 800 of the illustrated embodiment generally comprises an inflatable cuff or body 802, which is configured to support a valve 104

(see FIG. 2A) that is coupled to the cuff 802. In some embodiments, the valve 104 is a tissue valve. In some embodiments, the tissue valve has a thickness equal to or greater than about 0.011 inches. In another embodiment, the tissue valve has a thickness equal to or greater than about 0.018 inches. As will be explained in more detail below, the valve 104 is configured to move in response to the hemodynamic movement of the blood pumped by the heart 10 between an "open" configuration where blood can throw the implant 800 in a first direction (labeled A in FIG. 2B) and a "closed" configuration whereby blood is prevented from back flowing through the valve 104 in a second direction B (labeled B in FIG. 2B).

In the illustrated embodiment, the cuff 802 comprises a thin flexible tubular material such as a flexible fabric or thin membrane with little dimensional integrity. As will be explained in more detail below, the cuff 802 can be changed preferably, in situ, to a support structure to which other components (e.g., the valve 104) of the implant 800 can be secured and where tissue ingrowth can occur. Uninflated, the cuff 802 is preferably incapable of providing support. In one embodiment, the cuff 802 comprises Dacron, PTFE, ePTFE, TFE or polyester fabric as seen in conventional devices such as surgical stented or stent less valves and annuloplasty rings. The fabric thickness may range from about 0.002 inches to about 0.020 inches depending upon material selection and weave. Weave density may also be adjusted from a very tight weave to prevent blood from penetrating through the fabric to a looser weave to allow tissue to grow and surround the fabric completely. In preferred embodiments, the fabric may have a linear mass density about 20 denier or lower.

Figure 3B:
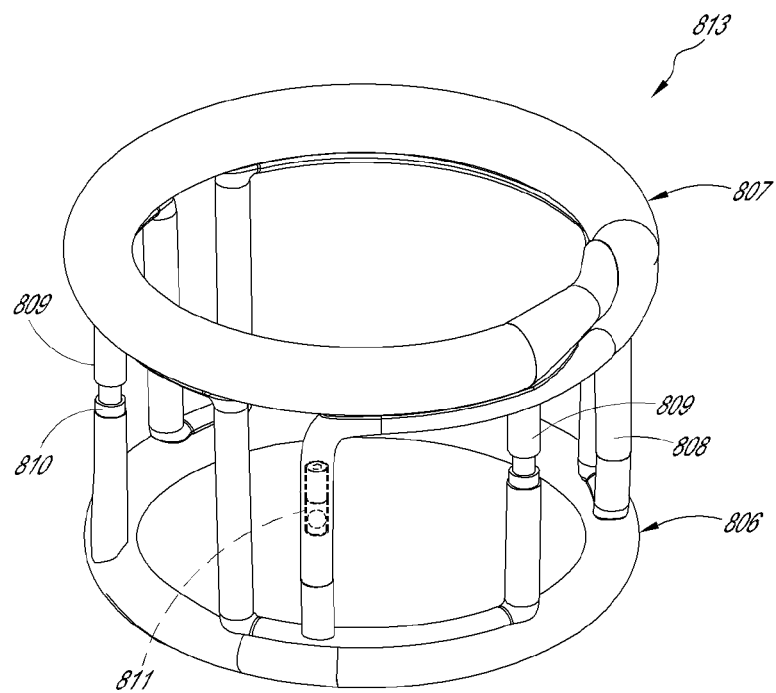
FIG. 3B is a front perspective view of an inflatable support structure of the implant of FIG. 3A.
Figure 3C:
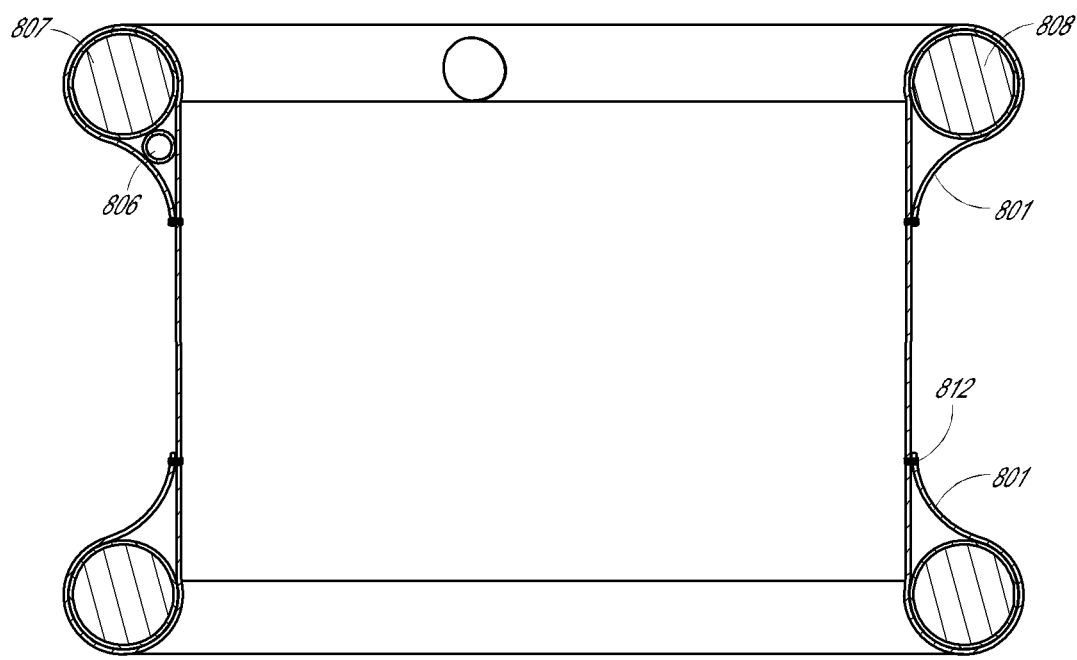
FIG. 3C is a cross-sectional side view of the implant of FIG. 3A.
Figure 3D:
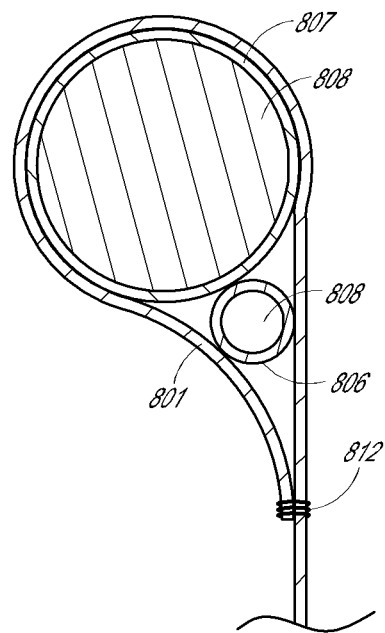
FIG. 3D is an enlarged cross-sectional view of an upper portion of FIG. 3C.

With reference to FIGS. 3B-3D, in the illustrated embodiment, the implant 800 includes an inflatable structure 813 that is formed by one or more inflation channels 808. The inflatable channels 808 are formed by a pair of distinct balloon rings or toroids (807a and 807b) and struts 806. In the illustrated embodiment, the implant 800 comprises a proximal toroid 807a at the proximal end 803 of the cuff 802 and a distal toroid 807b at the distal end 804 of the cuff 802. The toroids 807 can be secured to the cuff 802 in any of a variety of manners. With reference to FIGS. 3C and 3D, in the illustrated embodiment, the toroids 807 are secured within folds 801 formed at the proximal end 803 and the distal end 804 of the cuff 802. The folds 801, in turn, are secured by sutures or stitches 812. When inflated, the implant 800 is supported in part by series of struts 806 surrounding the cuff 802. In some embodiments, the struts 806 are configured so that the portions on the cuff run substantially perpendicular to the toroids. In some embodiments, the struts are sewn onto the cuff 802 or are enclosed in lumens made from the cuff material and swan onto the cuff 802. The toroids 807 and the struts 806 together form one or more inflatable channels 808 that can be inflated by air, liquid or inflation media.

With reference to FIG. 3B, the inflation channels are configured so that the cross-sectional profile of the implant 800 is reduced when it is compressed or in the retracted state. The inflation channels 808 are arranged in a step-function pattern. The inflation channels 808 have three connection ports 809 for coupling to the delivery catheter 900 via position and fill lumen tubing (PFL) tubing 916 (see FIGS. 5A-5C). In some embodiments, at least two of the connection ports 809 also function as inflation ports, and inflation media, air or liquid can be introduced into the inflation channel 808 through these ports. The PFL tubing 916 can be connected to the connection ports 809 via suitable connection mechanisms. In one embodiment, the connection between the PFL tubing 916 and the connection port 809 is a screw connection. In some embodiments, an inflation valve 810 is present in the connection port 809 and can stop the inflation media, air or liquid from escaping the inflation channels 808 after the PFL tubing is disconnected. In some embodiments, the distal toroid 807b and the proximal toroid 807a may be inflated independently. In some embodiments, the distal toroid 807b can be inflated separately from the struts 806 and the proximal toroid 807a. The separate inflation is useful during the positioning of the implant at the implantation site. With reference to FIGS. 3C and 3D, in some embodiments, the portion of struts 806 that runs parallel to the toroids 807 is encapsulated within the folds 801 of the implant 800. This may also aid in reducing the cross-sectional profile when the implant is compressed or folded.

As mentioned above, the inflatable rings or toroids 807 and struts 806 form the inflatable structure 813, which, in turn, defines the inflation channels 808. The inflation channels 808 receive inflation media to generally inflate the inflatable structure 813. When inflated, the inflatable rings 807 and struts 806 can provide structural support to the inflatable implant 800 and/or help to secure the implant 800 thin the heart 10. Uninflated, the implant 800 is a generally thin, flexible shapeless assembly that is preferably uncapable of support and is advantageously able to take a small, reduced profile form in which it can be percutaneously inserted into the body. As will be explained in more detail below, in modified embodiments, the inflatable structure 813 may comprise any of a variety of configurations of inflation channels 808 that can be formed from other inflatable members in addition to or in the alternative to the inflatable rings 807 and struts 806 shown in FIGS. 3A and 3B. In one embodiment, the valve has an expanded diameter that is greater than or equal to 22 millimeters and a maximum compressed diameter that is less than or equal to 6 millimeters (18 F).

With particular reference to FIG. 3B, in the illustrated embodiment, the distal ring 807b and struts 806 are joined such that the inflation channel 808 of the distal ring 807b is in fluid communication with the inflation channel 808 of some of the struts 806. The inflation channel 808 of the proximal ring 807a is also in communication with the inflation channels 808 of the proximal ring 807a and a few of the struts 806. In this manner, the inflation channels of the (i) proximal ring 807a and a few struts 806 can be inflated independently from the (ii) distal ring 807b and some struts. In some embodiments, the inflation channel of the proximal ring 807a is in communication with the inflation channel of the struts 806, while the inflation channel of the distal ring 807b is not in communication with the inflation channel of the struts. As will be explained in more detail below, the two groups of inflation channels 808 are preferably connected to independent PFL tubing 916 to facilitate the independent inflation. It should be appreciated that in modified embodiments the inflatable structure can include less (i.e., one common inflation channel) or more independent inflation channels. For example, in one embodiment, the inflation channels of the proximal ring 807a, struts 806 and distal ring 807b can all be in fluid communication with each other such that they can be inflated from a single inflation device. In another embodiment, the inflation channels of the proximal ring 807a, struts 806 and distal ring 807b can all be separated and therefore utilize three inflation devices.

With reference to FIG. 3B, in the illustrated embodiment, each of the proximal ring 807a and the distal ring 807b has a cross-sectional diameter of about 0.090 inches. The struts have a cross-sectional diameter of about 0.060 inches. In some embodiments, within the inflation channels 808 are also housed valve systems that allow for pressurization without leakage or passage of fluid in a single direction. In the illustrated embodiment shown in FIG. 3B, two end valves or inflation valves 810 reside at each end section of the inflation channels 808 adjacent to the connection ports 809. These end valves 810 are utilized to fill and exchange fluids such as saline, contrast agent and inflation media. The length of this inflation channel 808 may vary depending upon the size of the implant 800 and the complexity of the geometry. The inflation channel material may be blown using heat and pressure from materials such as nylon, polyethylene, Pebax, polypropylene or other common materials that will maintain pressurization. The fluids that are introduced are used to create the support structure, where without them, the implant 800 is an undefined fabric and tissue assembly. In one embodiment the inflation channels 808 are first filled with saline and contrast agent for radiopaque visualization under fluoroscopy. This can make positioning the implant 800 at the implantation site easier. This fluid is introduced from the proximal end of the catheter 900 with the aid of an inflation device such as an endoflator or other means to pressurize fluid in a controlled manner. This fluid is transferred from the proximal end of the catheter 900 through the PFL tubes 916 which are connected to the implant 800 at the end of each inflation channel 808 at the connection port 809.

With reference to FIG. 3B, in the illustrated embodiment, the inflation channel 808 can have an end valve 810 (i.e., inflation valve) at each end whereby they can be separated from the PFL tubes 916 thus disconnecting the catheter from the implant. This connection can be a screw or threaded connection, a colleting system, an interference fit or other means of reliable securement between the two components (i.e., the end valve 810 and the PFL tubes 916). In between the ends of the inflation channel 808 is an additional directional valve 811 to allow fluid to pass in a single direction. This allows for the filling of each end of the inflation channel 808 and displacement of fluid in a single direction. Once the implant 808 is placed at the desired position while inflated with saline and contrast agent, this fluid can be displaced by an inflation media that can solidify or harden. As the inflation media is introduced from the proximal end of the catheter 900, the fluid containing saline and contrast agent is pushed out from one end of the inflation channel 808. Once the inflation media completely displaces the first fluid, the PFL tubes are then disconnected from the implant 800 while the implant 800 remains inflated and pressurized. The pressure is maintained in the implant 800 by the integral valve (i.e., end valve 810) at each end of the inflation channel 808. In the illustrated embodiment, this end valve 810 has a ball 303 and seat to allow for fluid to pass when connected and seal when disconnected. In some case the implant 800 has three or more connection ports 809, but only two have inflation valves 810 attached. The connection port without the end valve 810 may use the same attachment means such as a screw or threaded element. Since this connection port is not used for communication with the support structure 813 and its filling, no inflation valve 810 is necessary. In other embodiments, all three connection ports 809 may have inflation valves 810 for introducing fluids or inflation media.

Figure 4:
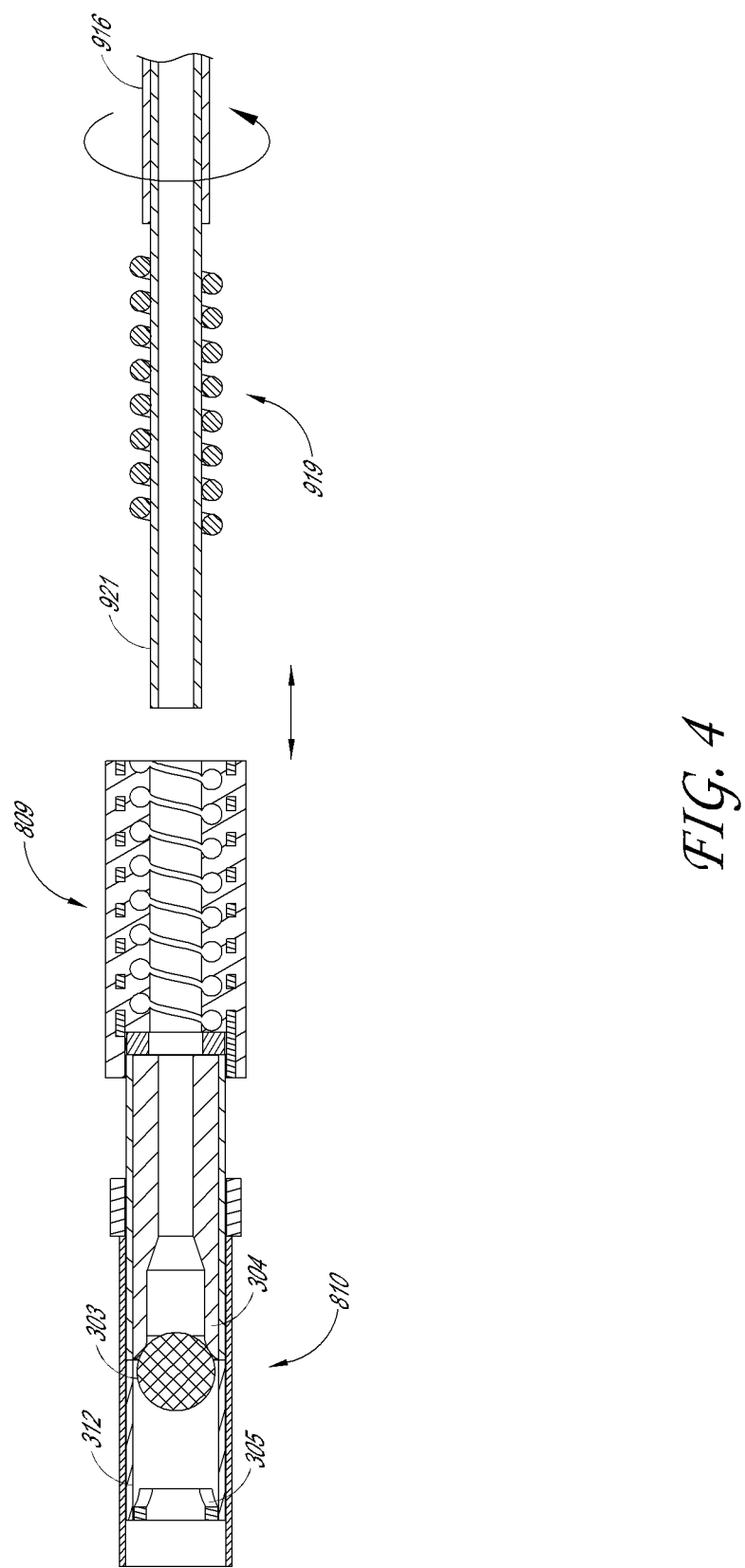
FIG. 4 is a cross-sectional view of the connection port and the inflation valve in the implant of FIG. 3B.

With reference to FIG. 4, the end valve system 810 comprises a tubular section 312 with a soft seal 304 and spherical ball 303 to create a sealing mechanism 313. The tubular section 312 in one embodiment is about 0.5 cm to about 2 cm in length and has an outer diameter of about 0.010 inches to about 0.090 inches with a wall thickness of about 0.005 inches to about 0.040 inches. The material may include a host of polymers such as nylon, polyethylene, Pebax, polypropylene or other common materials such as stainless steel, Nitinol or other metallic materials used in medical devices. The soft seal material may be introduced as a liquid silicone or other material where a curing occurs thus allowing for a through hole to be constructed by coring or blanking a central lumen through the seal material. The soft seal 304 is adhered to the inner diameter of the wall of the tubular member 312 with a through hole for fluid flow. The spherical ball 303 is allowed to move within the inner diameter of the tubular member 312 where it seats at one end sealing pressure within the inflation channels and is moved the other direction with the introduction of the PFL tube 916 but not allowed to migrate too far as a stop ring or ball stopper 305 retains the spherical ball 303 from moving into the inflation channel 808. As the PFL tube 916 is screwed into the connection port 809, the spherical ball 303 is moved into an open position to allow for fluid communication between the inflation channel 808 and the PFL tube 916. When disconnected, the ball 303 is allowed to move against the soft seal 304 and halt any fluid communication external to the inflation channel 808 leaving the implant 800 pressurized. Additional embodiments may utilize a spring mechanism to return the ball to a sealed position and other shapes of sealing devices may be used rather than a spherical ball. A duck-bill style sealing mechanism or flap valve would additionally suffice to halt fluid leakage and provide a closed system to the implant. Additional end valve systems have been described in U.S. Patent Publication No. 2009/0088836 to Bishop et al., which is thereby incorporated by reference herein.

The implant 800 allows the physician to deliver a prosthetic valve via catheterization in a lower profile and a safer manner than currently available. When the implant 800 is delivered to the site via a delivery catheter 900, the implant 800 is a thin, generally shapeless assembly in need of structure and definition. At the implantation site, the inflation media (e.g., a fluid or gas) may be added via PFL tubes of the delivery catheter 900 to the inflation channels 808 providing structure and definition to the implant 800. The inflation media therefore comprises part of the support structure for implant 800 after it is inflated. The inflation media that is inserted into the inflation channels 808 can be pressurized and/or can solidify in situ to provide structure to the implant 800. Additional details and embodiments of the implant 800, can be found in U.S. Pat. No. 5,554,185 to Block and U.S. Patent Publication No. 2006/0088836 to Bishop et al., the disclosures of which are expressly incorporated by reference in their entirety herein.

The cuff 802 may be made from many different materials such as Dacron, TFE, PTFE, ePTFE, woven metal fabrics, braided structures, or other generally accepted implantable materials. These materials may also be cast, extruded, or seamed together using heat, direct or indirect, sintering techniques, laser energy sources, ultrasound techniques, molding or thermoforming technologies. Since the inflation channels 808 generally surrounds the cuff 802, and the inflation channels 808 can be formed by separate members (e.g., balloons and struts), the attachment or encapsulation of these inflation channels 808 can be in intimate contact with the cuff material. In some embodiments, the inflation channels 808 are encapsulated in the folds 801 or lumens made from the cuff material sewn to the cuff 802. These inflation channels 808 can also be formed by sealing the cuff material to create an integral lumen from the cuff 802 itself. For example, by adding a material such as a silicone layer to a porous material such as Dacron, the fabric can resist fluid penetration or hold pressures if sealed. Materials may also be added to the sheet or cylinder material to create a fluid-tight barrier.

Various shapes of the cuff 802 may be manufactured to best fit anatomical variations from person to person. As described above, these may include a simple cylinder, a hyperboloid, a device with a larger diameter in its mid portion and a smaller diameter at one or both ends, a funnel type configuration or other conforming shape to native anatomies. The shape of the implant 800 is preferably contoured to engage a feature of the native anatomy in such a way as to prevent the migration of the device in a proximal or distal direction. In one embodiment the feature that the device engages is the aortic root or aortic bulb 34 (see e.g., FIG. 2A), or the sinuses of the coronary arteries. In another embodiment the feature that the device engages is the native valve annulus, the native valve or a portion of the native valve. In certain embodiments, the feature that the implant 800 engages to prevent migration has a diametral difference between 1% and 10%. In another embodiment, the feature that the implant 800 engages to prevent migration the a diameter difference is between 5% and 40%. In certain embodiments the diameter difference is defined by the free shape of the implant 800. In another embodiment the diameter difference prevents migration in only one direction. In another embodiment, the diameter difference prevents migration in two directions, for example proximal and distal or retrograde and antigrade. Similar to surgical valves, the implant 800 will vary in diameter ranging from about 14 mm to about 30 mm and have a height ranging from about 10 mm to about 30 mm in the portion of the implant 800 where the leaflets of the valve 104 are mounted. Portions of the implant 800 intended for placement in the aortic root may have larger diameters preferably ranging from about 20 mm to about 45 mm. In some embodiment, the implant 800 has an outside diameter greater than about 22 mm when fully inflated.

In certain embodiments, the cuffs, inflated structure can conform (at least partially) to the anatomy of the patient as the implant 800 is inflated. Such an arrangement may provide a better seal between the patient's anatomy and the implant 800.

Different diameters of prosthetic valves will be needed to replace native valves of various sizes. For different locations in the anatomy, different lengths of prosthetic valves or anchoring devices will also be required. For example a valve designed to replace the native aortic valve needs to have a relatively short length because of the location of the coronary artery ostium (left and right arteries). A valve designed to replace or supplement a pulmonary valve could have significantly greater length because the anatomy of the pulmonary artery allows for additional length. Different anchoring mechanisms that may be useful for anchoring the implant 800 have been described in U.S. Patent Publication No. 2009/0088836 to Bishop et al.

In the embodiments described herein, the inflation channels 808 may be configured such that they are of round, oval, square, rectangular or parabolic shape in cross section. Round cross sections may vary from about 0.020-about 0.100 inches in diameter with wall thicknesses ranging from about 0.0005-about 0.010 inches. Oval cross sections may have an aspect ratio of two or three to one depending upon the desired cuff thickness and strength desired. In embodiments in which the inflation channels 808 are formed by balloons, these channels 808 can be constructed from conventional balloon materials such as nylon, polyethylene, PEEK, silicone or other generally accepted medical device material In some embodiments, portions of the cuff or body 802 can be radio-opaque to aid in visualizing the position and orientation of the implant 800. Markers made from platinum gold or tantalum or other appropriate materials may be used. These may be used to identify critical areas of the valve that must be positioned appropriately, for example the valve commissures may need to be positioned appropriately relative to the coronary arteries for an aortic valve. Additionally during the procedure it may be advantageous to catheterize the coronary arteries using radio-opaque tipped guide catheters so that the ostia can be visualized. Special catheters could be developed with increased radio-opacity or larger than standard perfusion holes. The catheters could also have a reduced diameter in their proximal section allowing them to be introduced with the valve deployment catheter.

As mentioned above, during delivery, the body 802 is limp and flexible providing a compact shape to fit inside a delivery sheath. The body 802 is therefore preferably made form a thin, flexible material that is biocompatible and may aid in tissue growth at the interface with the native tissue. A few examples of material may be Dacron, ePTFE, PTFE, TFE, woven material such as stainless steel, platinum, MP35N, polyester or other implantable metal or polymer. As mentioned above with reference to FIG. 2A, the body 802 may have a tubular or hyperboloid shape to allow for the native valve to be excluded beneath the wall of the cuff 802. Within this cuff 802 the inflation channels 808 can be connected to a catheter lumen for the delivery of an inflation media to define and add structure to the implant 800. The valve 104, which is configured such that a fluid, such as blood, may be allowed to flow in a single direction or limit flow in one or both directions, is positioned within the cuff 802. The attachment method of the valve 104 to the cuff 802 can be by conventional sewing, gluing, welding, interference or other means generally accepted by industry.

In one embodiment, the cuff 802 would have a diameter of between about 15 mm and about 30 mm and a length of between about 6 mm and about 70 mm. The wall thickness would have an ideal range from about 0.01 mm to about 2 mm. As described above, the cuff 802 may gain longitudinal support in situ from members formed by inflation channels or formed by polymer or solid structural elements providing axial separation. The inner diameter of the cuff 802 may have a fixed dimension providing a constant size for valve attachment and a predictable valve open and closure function. Portions of the outer surface of the cuff 802 may optionally be compliant and allow the implant 800 to achieve interference fit with the native anatomy.

The implant 800 can have various overall shapes (e.g., an hourglass shape to hold the device in position around the valve annulus, or the device may have a different shape to hold the device in position in another portion of the native anatomy, such as the aortic root). Regardless of the overall shape of the implant 800, the inflatable channels 808 can be located near the proximal and distal ends 803, 804 of the implant 800, preferably forming a configuration that approximates a ring or toroid 807. These channels may be connected by intermediate channels designed to serve any combination of three functions: (i) provide support to the tissue excluded by the implant 800, (ii) provide axial and radial strength and stiffness to the 800, and/or (iii) to provide support for the valve 104. The specific design characteristics or orientation of the inflatable structure 813 can be optimized to better serve each function. For example if an inflatable channel 808 were designed to add axial strength to the relevant section of the device, the channels 808 would ideally be oriented in a substantially axial direction.

The cuff 802 and inflation channels 808 of the implant 800 can be manufactured in a variety of ways. In one embodiment the cuff 802 is manufactured from a fabric, similar to those fabrics typically used in endovascular grafts or for the cuffs of surgically implanted prosthetic heart valves. The fabric is preferably woven into a tubular shape for some portions of the cuff 802. The fabric may also be woven into sheets. In one embodiment, the yarn used to manufacture the fabric is preferably a twisted yarn, but monofilament or braided yarns may also be used. The useful range of yarn diameters is from approximately 0.0005 of an inch in diameter to approximately 0.005 of an inch in diameter. Depending on how tight the weave is made. Preferably, the fabric is woven with between about 50 and about 500 yarns per inch. In one embodiment, a fabric tube is woven with a 18 mm diameter with 200 yarns per inch or picks per inch. Each yarn is made of 20 filaments of a PET material. The final thickness of this woven fabric tube is 0.005 inches for the single wall of the tube. Depending on the desired profile of the implant 800 and the desired permeability of the fabric to blood or other fluids different weaves may be used. Any biocompatible material may be used to make the yarn, some embodiments include nylon and PET. Other materials or other combinations of materials are possible, including Teflon, floropolymers, polyimide, metals such as stainless steel, titanium, Nitinol, other shape memory alloys, alloys comprised primarily of a combinations of cobalt, chromium, nickel, and molybdenum. Fibers may be added to the yarn to increases strength or radiopacity, or to deliver a pharmaceutical agent. The fabric tube may also be manufactured by a braiding process.

The fabric can be stitched, sutured, sealed, melted, glued or bonded together to form the desired shape of the implant 800. The preferred method for attaching portions of the fabric together is stitching. The preferred embodiment uses a polypropylene monofilament suture material, with a diameter of approximately 0.005 of an inch. The suture material may range from about 0.001 to about 0.010 inches in diameter. Larger suture materials may be used at higher stress locations such as where the valve commissures attach to the cuff. The suture material may be of any acceptable implant grade material. Preferably a biocompatible suture material is used such as polypropylene. Nylon and polyethylene are also commonly used suture materials. Other materials or other combinations of materials are possible, including Teflon, fluoropolymers, polyimides, metals such as stainless steel, titanium, Kevlar, Nitinol, other shape memory alloys, alloys comprised primarily of a combinations of cobalt, chromium, nickel, and molybdenum such as MP35N. Preferably the sutures are a monofilament design. Multi strand braided or twisted suture materials also may be used. Many suture and stitching patterns are possible and have been described in various texts. The preferred stitching method is using some type of lock stitch, of a design such that if the suture breaks in a portion of its length the entire running length of the suture will resist unraveling. And the suture will still generally perform its function of holding the layers of fabric together.

In some embodiments, the implant 800 is not provided with separate balloons, instead the fabric of the cuff 802 itself can form the inflation channels 808. For example, in one embodiment two fabric tubes of a diameter similar to the desired final diameter of the implant 800 are place coaxial to each other. The two fabric tubes are stitched, fused, glued or otherwise coupled together in a pattern of channels 808 that is suitable for creating the geometry of the inflatable structure 813. In some embodiments, the fabric tubes are sewn together in a pattern so that the proximal and distal ends of the fabric tubes form an annular ring or toroid 807. In some embodiments, the middle section of the implant 800 contains one or more inflation channels shaped in a step-function pattern. In some embodiments, the fabric tubes are sewn together at the middle section of the implant to form inflation channels 808 that are perpendicular to the toroids 807 at the end sections of the implant 800. Methods for fabricating the implant 800 have been described in U.S. Patent Publication No. 2006/0088836 to Bishop et al.

In the illustrated embodiment of FIGS. 3A and 3B, the struts 806 are arranged such that there is no radial overlap with the distal and proximal rings 807a, 807b.

That is, in the illustrated embodiment, the struts 808 do not increase the radial thickness of the inflation structure because there is no radial overlap between the distal and proximal rings and the channels so that the channels lie within the radial thickness envelop defined by the distal and proximal rings 807a, 807b. In another embodiment, the struts 808 can be wider in the radial direction than the distal and proximal rings 807a, 807b such that the distal and proximal rings 807a, 807b lie within a radial thickness envelop defined by the struts 806.

In one embodiment, the valve 800 can be delivered through a deployment catheter with an 18 F or smaller outer diameter and when fully inflated has an effective orifice area of at least about 1.0 square cm; and in another embodiment at least about 1.3 square cm and in another embodiment about 1.5 square cm. In one embodiment, the valve 800 has a minimum cross-sectional flow area of at least about 1.75 square cm.

Leaflet Subassembly

With reference back to the embodiments of FIG. 2A, the valve 104 preferably is a tissue-type heart valve that includes a dimensionally stable, pre-aligned tissue leaflet subassembly. Pursuant to this construction, an exemplary tissue valve 104 includes a plurality of tissue leaflets that are templated and attached together at their tips to form a dimensionally stable and dimensionally consistent coapting leaflet subassembly. Then, in what can be a single process, each of the leaflets of the subassembly is aligned with and individually sewn to the cuff 802, from the tip of one commissure uniformly, around the leaflet cusp perimeter, to the tip of an adjacent commissure. As a result, the sewed sutures act like similarly aligned staples, all of which equally take the loading force acting along the entire cusp of each of the pre-aligned, coapting leaflets. Once inflated, the cuff 802 supports the commissures with the inflation media and its respective pressure which will solidify and create a system similar to a stent structure. The resulting implant 800 thereby formed can reduce stress and potential fatigue at the leaflet suture interface by distributing stress evenly over the entire leaflet cusp from commissure to commissure. In some embodiments, the tissue valve is coupled to the inflatable cuff 802 by attaching to the fabric of the cuff only.

In one embodiment, the tissue leaflets are not coupled to each other but are instead individually attached to the cuff 802.

A number of additional advantages result from the use of the implant 800 and the cuff 802 construction utilized therein. For example, for each key area of the cuff 802, the flexibility can be optimized or customized. If desired, the coapting tissue leaflet commissures can be made more or less flexible to allow for more or less deflection to relieve stresses on the tissue at closing or to fine tune the operation of the valve. Similarly, the base radial stiffness of the overall implant structure can be increased or decreased by pressure or inflation media to preserve the roundness and shape of the implant 800.

Attachment of the valve 104 to the cuff 802 can be completed in any number of conventional methods including sewing, ring or sleeve attachments, gluing, welding, interference fits, bonding through mechanical means such as pinching between members. An example of these methods are described in Published Applications from Huynh et al (06/102944) or Lafrance et al (2003/0027332) or U.S. Pat. No. 6,409,759 to Peredo, which are hereby incorporated by reference herein. These methods are generally know and accepted in the valve device industry. The valve, whether it is tissue, engineered tissue, mechanical or polymer, may be attached before packaging or in the hospital just before implantation. Some tissue valves are native valves such as pig, horse, cow or native human valves. Most of which are suspended in a fixing solution such as Glutaraldehyde.

In some embodiments, heart valve prostheses can be constructed with flexible tissue leaflets or polymer leaflets. Prosthetic tissue heart valves can be derived from, for example, porcine heart valves or manufactured from other biological material, such as bovine or equine pericardium. Biological materials in prosthetic heart valves generally have profile and surface characteristics that provide laminar, nonturbulent blood flow. Therefore, intravascular clotting is less likely to occur than with mechanical heart valve prostheses.

Natural tissue valves can be derived from an animal species, typically mammalian, such as human, bovine, porcine canine, seal or kangaroo. These tissues can be obtained from, for example, heart valves, aortic roots, aortic walls, aortic leaflets, pericardial tissue such as pericardial patches, bypass grafts, blood vessels, human umbilical tissue and the like. These natural tissues are typically soft tissues, and generally include collagen containing material. The tissue can be living tissue, decellularized tissue or recellularized tissue. Tissue can be fixed by crosslinking. Fixation provides mechanical stabilization, for example by preventing enzymatic degradation of the tissue. Glutaraldehyde or formaldehyde is typically used for fixation, but other fixatives can be used, such as other difunctional aldehydes, epoxides, genipin and derivatives thereof. Tissue can be used in either crosslinked or uncrosslinked form, depending on the type of tissue, use and other factors. Generally, if xenograft tissue is used, the tissue is crosslinked and/or decellularized. Additional description of tissue valves can be found in U.S. Patent Publication No. 2009/008836 to Bishop et al.

Inflation Media

The inflatable structure 813 can be inflated using any of a variety of inflation media, depending upon the desired performance. In general, the inflation media can include a liquid such water or an aqueous based solution, a gas such as $CO_2$, or a hardenable media which may be introduced into the inflation channels 808 at a first, relatively low viscosity and converted to a second, relatively high viscosity. Viscosity enhancement may be accomplished through any of a variety of known UV initiated or catalyst initiated polymerization reactions, or other chemical systems known in the art. The end point of the viscosity enhancing process may result in a hardness anywhere from a gel to a rigid structure, depending upon the desired performance and durability.

Useful inflation media generally include those formed by the mixing of multiple components and that have a cure time ranging from a tens of minutes to about one hour, preferably from about twenty minutes to about one hour. Such a material may be biocompatible, exhibit long-term stability (preferably on the order of at least ten years in vivo), pose as little an embolic risk as possible, and exhibit adequate mechanical properties, both pre and post-cure, suitable for service in the cuff of the present invention in vivo. For instance, such a material should have a relatively low viscosity before solidification or curing to facilitate the cuff and channel fill process. A desirable post-cure elastic modulus of such an inflation medium is from about 50 to about 400 psi—balancing the need for the filled body to form an adequate seal in vivo while maintaining clinically relevant kink resistance of the cuff. The inflation media ideally should be radiopaque, both acute and chronic, although this is not absolutely necessary.

One preferred family of hardenable inflation media are two part epoxies. The first part is an epoxy resin blend comprising a first aromatic diepoxy compound and a second aliphatic diepoxy compound. The first aromatic diepoxy compound provides good mechanical and chemical stability in an aqueous environment while being soluble in aqueous solution when combined with suitable aliphatic epoxies. In some embodiments, the first aromatic diepoxy compound comprises at least one N,N-diglycidylaniline group or segment. In some embodiments, the first aromatic diepoxy compound are optionally substituted N,N-diglycidylaniline. The substitutent may be glycidyloxy or N,N-diglycidylanilinyl-methyl. Non-limiting examples of the first aromatic diepoxy compound are N,N-diglycidylaniline, N,N-diclycidyl-4-glycidyloxyaniline (DGO) and 4,4'-methylene-bis (N,N-diglycidylaniline) (MBD), etc.

The second aliphatic diepoxy compound provides low viscosity and good solubility in an aqueous solution. In some embodiments, the second aliphatic diepoxy compound may be 1,3-butadiene diepoxide, glycidyl ether or $C_{1-5}$ alkane diols of glycidyl ether. Non-limiting examples of the second aliphatic diepoxy compounds are 1,3-butadiene diepoxide, butanediol diglycidyl ether (BDGE), 1,2-ethanediol diglycidyl ether, glycidyl ether, etc.

In some embodiments, additional third compound may be added to the first part epoxy resin blend for improving mechanical properties and chemical resistance. In some embodiments, the additional third compound may be an aromatic epoxy other than the one containing N,N-diglycidylanaline. However, the solubility of the epoxy resin blend can also decrease and the viscosity can increase as the concentration of the additional aromatic epoxies increases. The preferred third compound may be tris(4-hydroxyphenyl)methane triglycidyl ether (THTGE), bisphenol A diglycidyl ether (BADGE), bisphenol F diglycidyl ether (BFDGE), or resorcinol diglycidyl ether (RDGE).

In some embodiments, the additional third compound may be a cycloaliphatic epoxy compound, preferably more soluble than the first aromatic diepoxy compound. It can increase the mechanical properties and chemical resistance to a lesser extent than the aromatic epoxy described above, but it will not decrease the solubility as much. Non-limiting examples of such cycloaliphatic epoxy are 1,4-cyclohexanedimethanol diclycidyl ether and cyclohexene oxide diglycidyl 1,2-cyclohexanedicarboxylate. Similarly, in some embodiments, aliphatic epoxy with 3 or more glycidyl ether groups, such as polyglycidyl ether, may be added as the additional third compound for the same reason. Polyglycidyl ether may increase cross linking and thus enhance the mechanical properties.

In general, the solubility of the epoxy resin blend decreases and the viscosity increases as the concentration of the first aromatic diepoxy compound increases. In addition, the mechanical properties and chemical resistance may be reduced as the concentration of the aliphatic diepoxy compound goes up in the epoxy resin blend. By adjusting the ratio of the first aromatic dipoxy compound and the second aliphatic diepoxy compound, a person skilled in the art can control the desired properties of the epoxy resin blend and the hardened media. Adding the third compound in some embodiments may allow further tailoring of the epoxy resin properties.

The second part of the hardenable inflation media comprises a hardener comprising at least one cycloaliphatic amine. It provides good combination of reactivity, mechanical properties and chemical resistance. The cycloaliphatic amine may include, but not limited to, isophorone diamine (IPDA), 1,3-bisaminocyclohexame (1,3-BAC), diamino cyclohexane (DACH), n-aminoethylpiperazine (AEP) or n-aminopropylpiperazine (APP).

In some embodiments, an aliphatic amine may be added into the second part to increase reaction rate, but may decrease mechanical properties and chemical resistance. The preferred aliphatic amine has the structural formula (I):

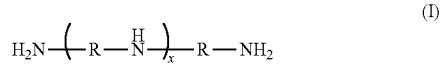

(I)

wherein each R is independently selected from branched or linear chains of $C_{2-5}$ alkyl, preferably $C_2$ alkyl. The term "alkyl" as used herein refers to a radical of a fully saturated hydrocarbon, including, but not limited to, methyl, ethyl, n-propyl, isopropyl (or i-propyl), n-butyl, isobutyl, tert-butyl (or t-butyl), n-hexyl, and the like. For example, the term "alkyl" as used herein includes radicals of fully saturated hydrocarbons defined by the following general formula $C_nH_{2n+2}$. In some embodiments, the aliphatic amine may include, but not limited to, tetraethylenepentamine (TEPA), diethylene triamine and triethylene tetraamine. In some embodiments, the hardener may further comprise at least one radio-opaque compound, such as iodo benzoic acids.

Additional details of hardenable inflation media are described in co-pending application titled "Inflation Media Formulation," hereby incorporated herein by reference. Other suitable inflation media are also described in U.S. patent application Ser. No. 09/496,231 to Hubbell et al., filed Feb. 1, 2000, entitled "Biomaterials Formed by Nucleophilic Addition Reaction to Conjugated Unsaturated Groups" and U.S. Pat. No. 6,958,212 to Hubbell et al. The entireties of each of these patents are hereby incorporated herein by reference.

Below is Listed One Particular Two-Component Medium. This Medium Comprises: First Part—Epoxy Resin Blend (1) N,N-Diglycidyl-4-glycidyloxyaniline (DGO), present in a proportion ranging from about 10 to about 70 weight percent; specifically in a proportion of about 50 weight percent, (2) Butanediol diglycidyl ether (BDGE) present in a proportion ranging from about 30 to about 75 weight percent; specifically in a proportion of about 50 weight percent, and optionally (3) 1,4-Cyclohexanedimethanol diglycidyl ether, present in a proportion ranging from about 0 to about 50 weight percent.

Second Part—Amine Hardener (1) Isophorone diamine (IPDA), present in a proportion ranging from about 75 to about 100 weight percent, and optionally (2) Diethylene triamine (DETA), present in a proportion ranging from about 0 to about 25 weight percent.

The mixed uncured inflation media preferably has a viscosity less than 2000 cps. In one embodiment the epoxy based inflation media has a viscosity of 100-200 cps.

In another embodiment the inflation media has a viscosity less than 1000 cps. In some embodiments, the epoxy mixture has an initial viscosity of less than about 50 cps, or less than about 30 cps after mixing. In some embodiments, the average viscosity during the first 10 minutes following mixing the two components of the inflation media is about 50 cps to about 60 cps. The low viscosity ensures that the inflation media can be delivered through the inflation lumen of a deployment catheter with small diameter, such as an 18 French catheter In some embodiments, the balloon or inflation channel may be connected to the catheter on both ends. This allows the balloon to be pre-inflated with a non-solidifying material such as a gas or liquid. If a gas is chosen, $CO_2$ or helium are the likely choices; these gasses are used to inflate intraortic balloon pumps. Preferably the pre-inflation media is radio-opaque so that the balloon position can be determined by angiography. Contrast media typically used in interventional cardiology could be used to add sufficient radio-opacity to most liquid pre-inflation media. When it is desired to make the implant permanent and exchange the pre-inflation media for the permanent inflation media, the permanent inflation media is injected into the inflation channel through a first catheter connection. In some embodiments, the permanent inflation media is capable of solidifying into a semi-solid, gel or solid state. As the permanent inflation media is introduced into the inflatable structure, the pre-inflation media is expelled out from a second catheter connection. The catheter connections are positioned in such a way that substantially all of the pre-inflation media is expelled as the permanent inflation media is introduced. In one embodiment an intermediate inflation media is used to prevent entrapment of pre-inflation media in the permanent inflation media. In one embodiment the intermediate inflation media is a gas and the pre-inflation media is a liquid. In another embodiment the intermediate inflation media or pre-inflation media functions as a primer to aid the permanent inflation media to bond to the inner surface of the inflation channel. In another embodiment the pre-inflation media or the intermediate inflation media serves as a release agent to prevent the permanent inflation media from bonding to the inner surface of the inflation channel.

The permanent inflation media may have a different radiopacity than the preinflation media. A device that is excessively radiopaque tends to obscure other nearby features under angiography. During the preinflation step it may be desirable to visualize the inflation channel clearly, so a very radiopaque inflation media may be chosen. After the device is inflated with the permanent inflation media a less radiopaque inflation media may be preferred. The feature of lesser radiopacity is beneficial for visualization of proper valve function as contrast media is injected into the ventricle or the aorta.

Another embodiment of the inflation media is disclosed in co-pending application filed on the same day as this application under Attorney Docket: DFMED.034A, entitled INFLATION MEDIA FOR IMPLANTS, and U.S. Provisional Patent Application No. 61/346,419 filed May 19, 2011, the entirety of these applications are hereby incorporated by reference herein.

Low Crossing Profile Delivery System

Figure 5A:
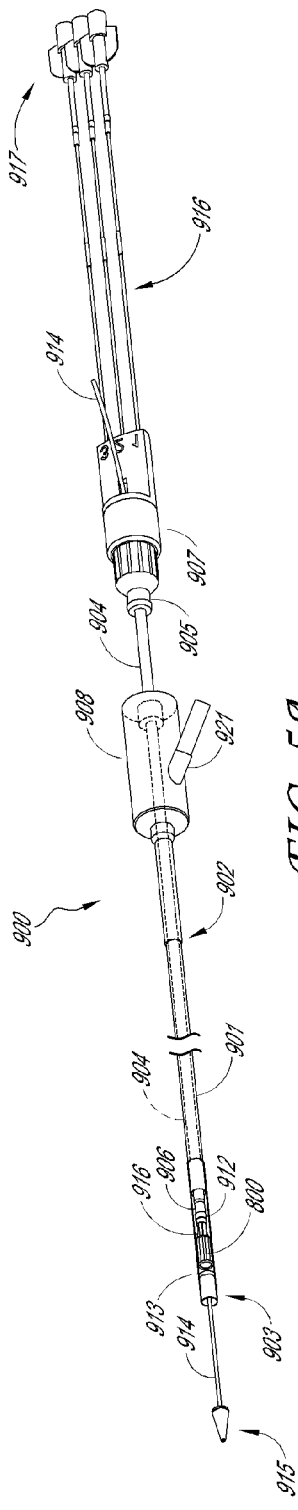
FIG. 5A is a side perspective view of a deployment catheter with retracted implant.
Figure 5B:
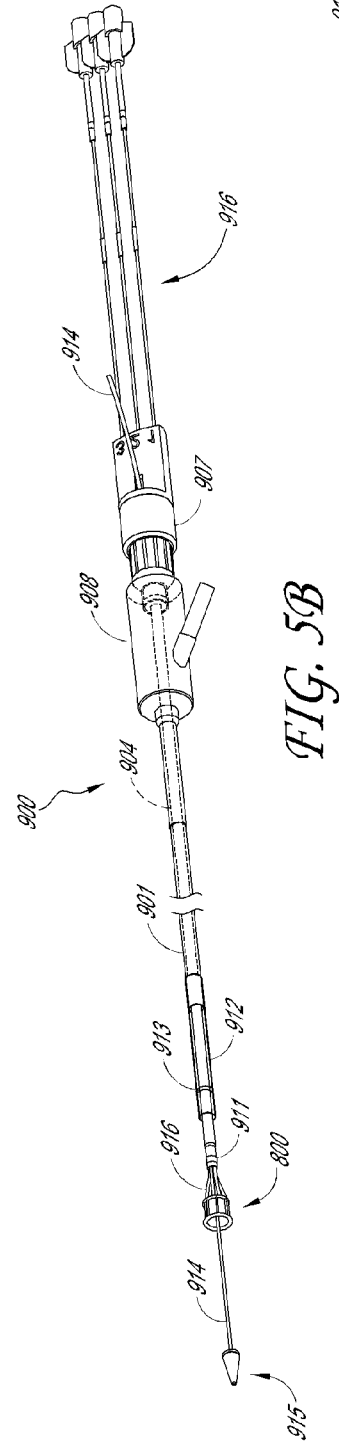
FIG. 5B is a side perspective view of the deployment catheter of FIG. 5A with the implant outside of the outer sheath jacket.

FIGS. 5A-5B illustrate an exemplary embodiment of a low crossing profile delivery catheter 900 that can be used to deliver the implant 800. In general, the delivery system comprises a delivery catheter 900, and the delivery catheter 900 comprises an elongate, flexible catheter body having a proximal end and a distal end. In some embodiments, the catheter body has an outer diameter of about 18 French or less particularly at the distal portion of the catheter body (i.e. the deployment portion). In some embodiments, the delivery catheter also comprises a cardiovascular prosthetic implant 800 at the distal end of the catheter body. As described herein, certain features of the implant 800 and delivery catheter 900 are particularly advantageous for facilitating delivering of cardiovascular prosthetic implant 800 an within a catheter body having outer diameter of about 18 French or less while still maintaining a tissue valve thickness equal to or greater than about 0.011 inches and/or having an effective orifice area equal to or greater than about 1 cm squared, or in another embodiment, 1.3 cm squared or in another embodiment 1.5 cm squared. In such embodiments, the implant 800 may also have an expanded maximum diameter that is greater than or equal to about 22 mm. In some embodiments, at least one link exists between the catheter body and the implant 800. In some embodiments, the at least one link is the PFL tubing. In one embodiment, the delivery system is compatible with 0.035" or 0.038" guidewire.

In general, the delivery catheter 900 can be constructed with extruded tubing using well known techniques in the industry. In some embodiments, the catheter 900 can incorporates braided or coiled wires and or ribbons into the tubing for providing stiffness and rotational torqueability. Stiffening wires may number between 1 and 64. In some embodiments, a braided configuration is used that comprises between 8 and 32 wires or ribbon. If wires are used in other embodiments, the diameter can range from about 0.0005 inches to about 0.0070 inches. If a ribbon is used, the thickness is preferably less than the width, and ribbon thicknesses may range from about 0.0005 inches to about 0.0070 inches while the widths may range from about 0.0010 inches to about 0.0100 inches. In another embodiment, a coil is used as a stiffening member. The coil can comprise between 1 and 8 wires or ribbons that are wrapped around the circumference of the tube and embedded into the tube. The wires may be wound so that they are parallel to one another and in the curved plane of the surface of the tube, or multiple wires may be wrapped in opposing directions in separate layers. The dimensions of the wires or ribbons used for a coil can be similar to the dimensions used for a braid.

With reference to FIGS. 5A and 5B, the catheter 900 comprises an outer tubular member 801 having a proximal end 902 and a distal end 903, and an inner tubular member 904 also having a proximal end 905 and a distal end 906. The inner tubular member 904 extends generally through the outer tubular member 901, such that the proximal and distal ends 902, 903 of the inner tubular member 904 extend generally past the proximal end 902 and distal end 903 of the outer tubular member 901. The distal end 903 of the outer tubular member 901 comprises a sheath jacket 912. In some embodiments, the sheath jacket 912 may comprise KYNAR tubing. The sheath jacket 912 can house the implant 800 in a retracted state for delivery to the implantation site. In some embodiments, the sheath jacket 912 is capable of transmitting at least a portion of light in the visible spectrum. This allows the orientation of the implant 800 to be visualized within the catheter 900. In some embodiments, an outer sheath marking band 913 may be located at the distal end 903 of the outer tubular member 901. The proximal end 905 of the inner tubular member 904 is connected to a handle 907 for grasping and moving the inner tubular member 904 with respect to the outer tubular member 901. The proximal end 902 of the outer tubular member 901 is connected to an outer sheath handle 908 for grasping and holding the outer tubular member 901 stationary with respect to the inner tubular member 904. A hemostasis seal 909 is preferably provided between the inner and outer tubular members 901, 904, and the hemostasis seal 909 is disposed in outer sheath handle 908. In some embodiments, the outer sheath handle 908 comprises a sideport valve 921, and the fluid can be passed into the outer tubular member through it.

Figure 6:
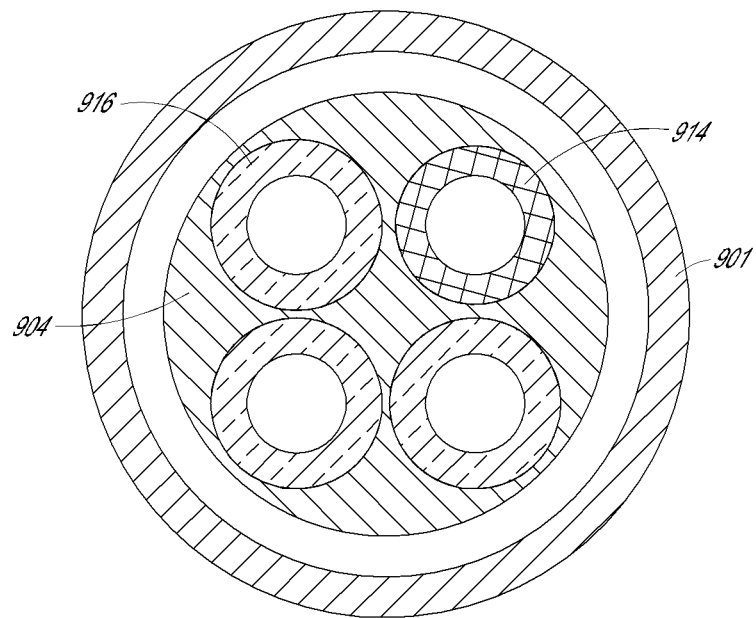
FIG. 6 is a cross-sectional view taken through line A-A of FIG. 5B.

In general, the inner tubular member 904 comprises a multilumen hypotube (see FIG. 6). In some embodiments, a neck section 910 is located at the proximal end 905 of the inner tubular member 904. The neck section 910 may be made from stainless steel, Nitinol or another suitable material which can serve to provide additional strength for moving the inner tubular member 904 within the outer tubular member 901. In some embodiments, a mulilumen marker band 911 is present at the distal end 906 of the inner tubular member 904. The multilumen hypotube has a wall thickness between about 0.004 in and about 0.006 in. In a preferred embodiment, the wall thickness is about 0.0055 in, which provides sufficient column strength and increases the bending load required to kink the hypotube. With reference to FIG. 6, the inner tubular member 904 (i.e., multilumen hypotube) comprises at least four lumens. One of the lumens accommodates the guidewire tubing 914, and each of the other lumens accommodates a positioning-and-fill lumen (PFL) tubing 916. The guidewire tubing 914 is configured to receive a guidewire. The PFL tubing 916 is configured to function both as a control wire for positioning the implant 800 at the implantation cite, and as an inflation tube for delivering a liquid, gas or inflation media to the implant 800. In particular, the tubing 916 can allow angular adjustment of the implant 800. That is, the plane of the valve (defined generally perpendicular to the longitudinal axis of the implant 800) can be adjusted with the tubing 916.

With reference to FIGS. 5A and 5B, in general, the guidewire tubing 914 is longer than and extends throughout the length of the delivery catheter 900. The proximal end of the guidewire tubing 914 passes through the inner sheath handle 907 for operator's control; the distal end of the guidewire tubing 914 extends past the distal end 903 of the outer tubular member 901, and is coupled to a guidewire tip 915. The guidewire tip 915 can close the distal end 903 of the outer tubular member 901 (or the receptacle) and protect the retracted implant 800, for example, during the advancement of the delivery catheter. The guidewire tip 915 can be distanced from the outer tubular member 901 by proximally retracting the outer tubular member 901 while holding the guidewire tubing 914 stationary. Alternatively, the guidewire tubing 914 can be advanced while holding the outer tubular member 901 stationary. The guidewire tubing 914 may have an inner diameter of about 0.035 inches to about 0.042 inches, so the catheter system is compatible with common 0.035" or 0.038" guidewires. In some embodiments, the guidewire tubing 914 may have an inner diameter of about 0.014 inches to about 0.017 inches, so the catheter system is compatible with a 0.014" diameter guidewire. The guidewire tubing 914 may be made from a lubricious material such as Teflon, polypropylene or a polymer impregnated with Teflon. It may also be coated with a lubricous or hydrophilic coating.

The guidewire tip 915 may be cone shaped, bullet shaped or hemispherical on the front end. The largest diameter of the guidewire tip 915 is preferably approximately the same as the distal portion 903 of the outer tubular member 901. The guidewire tip 915 preferably steps down to a diameter slightly smaller than the inside diameter of the outer sheath jacket 912, so that the tip can engage the outer sheath jacket 912 and provide a smooth transition. In the illustrated embodiment, the guidewire tip 915 is connected to the guidewire tube 914, and the guidewire lumen passes through a portion of the guidewire tip 915. The proximal side of the guidewire tip 915 also has a cone, bullet or hemispherical shape, so that the guidewire tip 915 can easily be retraced back across the deployed implant 800, and into the deployment catheter 900. The guidewire tip 915 can be manufactured from a rigid polymer such as polycarbonate, or from a lower durometer material that allows flexibility, such as silicone. Alternatively, the guidewire tip 915 may be made from multiple materials with different durometers. For example, the portion of the guidewire tip 915 that engages the distal portion 903 of the outer tubular member 901 can be manufactured from a rigid material, while the distal and or proximal ends of the guidewire tip 915 are manufactured from a lower durmoter material.

Figure 5C:
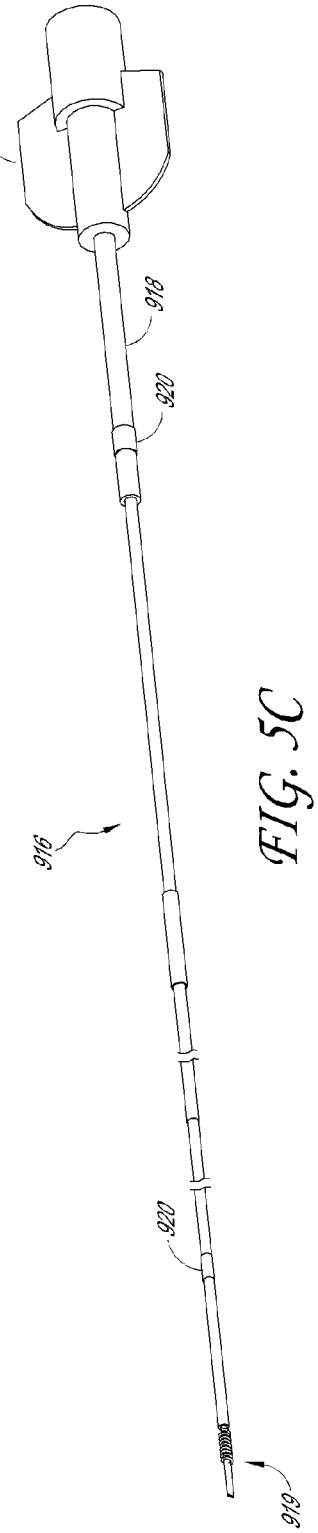
FIG. 5C is a side perspective view of the position-and-fill lumen (PFL), which is a component of the deployment catheter of FIGS. 5A and 5B.

Each PFL tubing 916 also extends throughout the length of the delivery catheter 900. The proximal end of the PFL tubing 916 passes through the handle 907, and has a luer lock 917 for connecting to fluid, gas or inflation media source. The distal end of the PFL tubing 916 extends past the distal end 906 of the inner tubular member 904 through the hypotube lumen. With reference to FIG. 5C, in some embodiments, the PFL tubing 916 comprises a strain relief section 918 at the proximal end where the tubing 916 is connected to the luer lock 917, and the strain relief section 918 serves to relieve the strain on the PFL tubing 916 while being maneuvered by the operator. The distal end of the PFL tubing 916 comprises a tip or needle 919 for connecting to the implant 800. In some embodiments, the tip 919 may have a threaded section toward the end of the needle 919 (see FIG. 5C). In some embodiments, the PFL tubing 916 may have PFL marker(s) 920 at the distal end and/or proximal end of the tubing 916 for identification.

The PFL tubing 916 is designed to accommodate for the ease of rotation in a tortuous anatomy. The tubing 916 may be constructed using polyimide braided tube, Nitinol hypotube, or stainless steel hypotube. In a preferred embodiment, the PFL tubing 916 is made from braided polyimide, which is made of polyimide liner braided with flat wires, encapsulated by another polyimide layer and jacketed with prebax and nylon outer layer. In some embodiments, a Nitinol sleeve may be added to the proximal end of the PFL tubing 916 to improve torque transmission, kinks resistance and pushability. In some embodiments, the outside surface of the PFL tubing 916 and/or the inside surface of the lumens in the multilumen hypotube can also be coated with a lubricious silicone coating to reduce friction. In some embodiments, an inner lining material such as Teflon may be used on the inside surface of the lumens in the multilumen hypotube to reduce friction and improve performance in tortuous curves. Additionally, slippery coatings such as DOW 360, MDX silicone or a hydrophilic coating from BSI Corporation may be added to provide another form of friction reducing elements. This can provide a precision control of the PFL tubings 916 during positioning of the implant 800. In some embodiments, the outside surface of the PFL tubing 916 can be jacketed and reflowed with an additional nylon 12 or Relsan AESNO layer to ensure a smooth finished surface. In some embodiments, anti-thrombus coating can also be put on the outside surface of the PFL tubing 916 to reduce the risk of thrombus formation on the tubing.

In some embodiments, the outer diameter of the catheter 900 measures generally about 0.030 inches to about 0.200 inches with a wall thickness of the outer tubular member 901 being about 0.005 inches to about 0.060 inches. In preferred embodiments, the outer diameter of the outer tubular member 901 is between about 0.215 and about 0.219 inches. In this embodiment, the wall thickness of the outer tubular member 901 is between about 0.005 inches and about 0.030 inches. The overall length of the catheter 900 ranges from about 80 centimeters to about 320 centimeters. In preferred embodiments, the working length of the outer tubular member 901 (from the distal end of the sheath jacket 912 to the location where the tubular member 901 is connected to the outer sheath handle 908) is about 100 cm to about 120 cm. In some embodiments, the inner diameter of the sheath jacket 912 is greater than or equal to about 0.218 inches, and the outer diameter of the sheath jacket 912 is less than or equal to about 0.241 inches. In a preferred embodiment, the outer diameter of the sheath jacket portion 912 is less than or equal to about 0.236 inches or 18 French. In some embodiments, the outer diameter of the PFL tubing 916 is less than or equal to about 0.0435 inches, and the length is about 140 cm to about 160 cm.

In the embodiments that employ a low crossing profile outer tubular member, a low profile inflatable implant in a retracted state is preferable for fitting into the sheath jacket 912. The low crossing profile outer tubular member may comprise an outer sheath with a sheath jacket 912 having an outer diameter of 18 French or less. In some embodiments, the implant 800 comprises a tissue valve 104 with an expanded outer diameter greater than or equal to about 22 mm and a tissue thickness of greater than or equal to about 0.011 inches. The compressed diameter of the implant 800 may be less than or equal to about 6 mm or 18 French. The retracted implant 800 is generally loaded between the distal portion 903 of the outer tubular member 901 and the distal portion 906 of the inner tubular member 904. The distal portion 903 of the outer tubular member 901 therefore forms a receptacle for the implant 800. The implant 800 may be exposed or pushed out of the receptacle by holding the implant 800 stationary as the outer tubular member 901 is retracted. Alternatively, the outer tubular member 901 can be held stationary while the inner tubular member 904 is advanced and thereby pushing the implant 800 out of the receptable.

Figure 7:
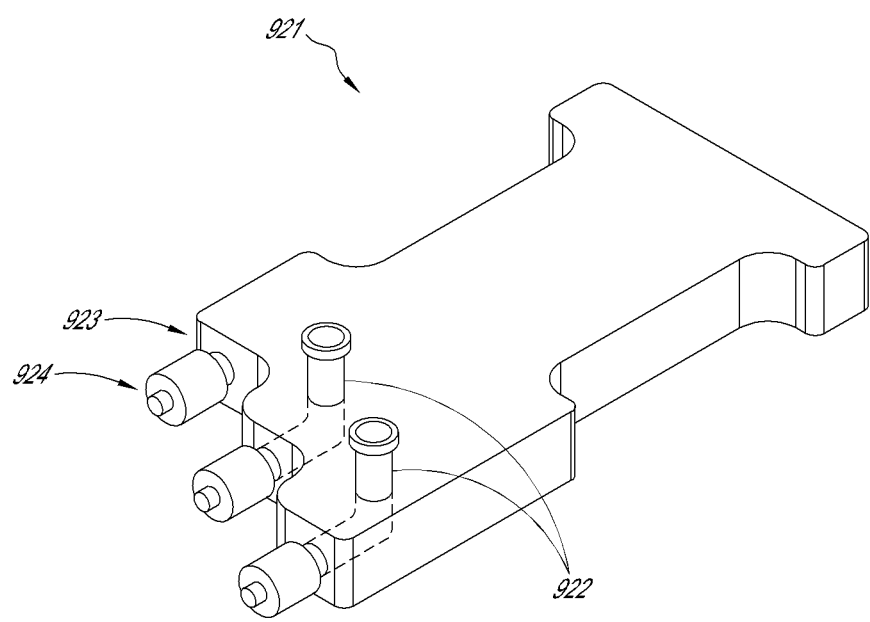
FIG. 7 is a side perspective view of a loading tool base.

The delivery system also includes a loading tool base 925 that is configured to connect to the PFL tubing 916. In some embodiments, the PFL tubing 916 can connect to the loading tool base 921 via a luer connection. With reference to FIG. 7, one end of the loading tool base 921 may be configured to have step edge 923s. In some embodiments, the distal end of the loading tool base has three step edges 923, each step edge 923 has a luer connector 924 for connecting the PFL tubing 916. In some embodiments, the loading tool base 921 may also comprise at least two additional connectors 922 (e.g. additional luer connectors), each in fluid communication with one of the luer connector 924 on the stepped edges 923, which would allow the introduction of fluid, gas or air into the implant 800 for testing purposes. For example, in the exemplified embodiment, once the PFL tubings 916 are connected to the loading tool base 921, a liquid or air source can be connected to the loading tool base 921 via the additional connectors 922. The liquid or air can then be introduced into the implant 800 through the loading tool base 921 and the PFL tubings 916.

Figure 12:
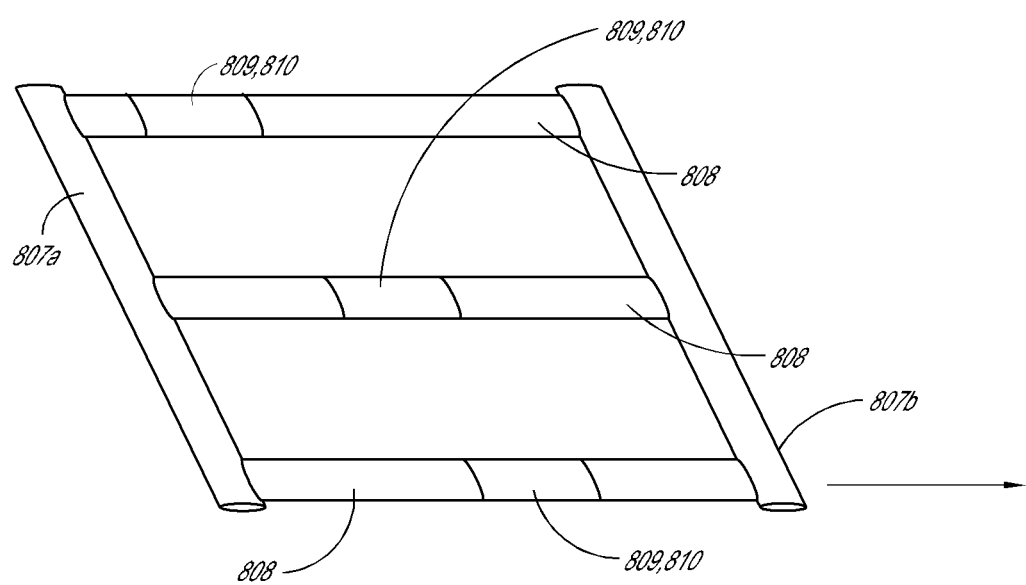
FIG. 12 is a side perspective view of a method of compressing the implant of FIGS. 3A-B.

The step edges 923 on the loading tool base 921 allows the implant 800 to be collapsed or folded up tightly so it can be loaded into the sheath jacket 912 at the distal end of the outer tubular member 901. When the proximal end of the PFL tubings 916 are connected to the loading tool base 921 and the distal end connected to the connection ports 809 of the implant 800, the step edge connections pull the PFL tubings 916 in a way that creates an offset of the inflation valves 810 and/or the connection ports 809 in the inflation channels 808 when the implant 800 is folded or collapsed. By staggering the connection ports/inflation valves, the collapsed implant 800 can have a reduced cross-sectional profile. In some embodiments, the check valve 814 in the inflation channel is also staggered with the connection ports/inflation valves in the collapsed state. Accordingly, in one embodiment, the inflation valves 810 and/or the connection ports 809 are axially aligned when the valve is positioned within the deployment catheter in a collapsed configuration. That is, the inflation valves 810 and/or the connection ports 809 and/or check valve 814 are positioned such that they do not overlap with each other but are instead aligned generally with respect to the longitudinal axis of the deployment catheter. In this manner, the implant 800 can be collapsed into a smaller diameter as opposed to a configuration in which with the inflation valves 810 and/or the connection ports 809 and/or check valve 814 overlap each other in a radial direction, which can increase the diameter of the compressed implant 800. In a similar manner, the channels 806 can be arranged positioned such hat they also do not overlap with each other as shown in FIG. 12. As shown in FIG. 12, the loading tool base 925 can be used to pull one end of the distal and proximal rings 807a, 807b in a proximal direction so as to align the inflation valves 810 and/or the connection ports 809 and/or check valve 814 axially as described above and/or align the channels so as to reduce the overlap between multiple channels 806.

Method of Deployment

The implant 800 may be deployed in the aortic position using the low crossing profile delivery system and a minimally invasive procedure. In some embodiments, the method generally comprises gaining access to the aorta, most often through the femoral artery. The vascular access site is prepared according to standard practice, and the guidewire is inserted into the left ventricle through the vascular access. In some embodiments, an introducer is placed in the access vessel. A balloon valvuloplasty may optionally be performed in the case of aortic stenosis.

The catheter 900 carrying the cardiovascular prosthetic implant is translumenally advanced to a position proximate a native valve. After the delivery sheath or catheter 900 is inserted over the guidewire and advanced over the aortic arch and past the aortic valve, the implant 800 may be reveled or exposed by retracting the outer tubular member 901 partially or completely while holding the inner tubular member 904 stationary and allowing proper placement at or beneath the native valve. In some embodiments, the implant may also be reveled by pushing the inner tubular member 904 distally while holding the outer tubular member 901 stationary. Once the implant 800 is unsheathed, it may be moved proximally or distally, and the fluid or inflation media may be introduced to the cuff 802 providing shape and structural integrity. In some embodiments, the distal toroid of the inflatable cuff or inflatable structure is inflated first with a first liquid, and the implant 800 is positioned at the implantation cite using the links between the implant 800 and the catheter 900. In some embodiments, no more than three links are present. In some embodiments, the links are PRL tubes 916, which can be used to both control the implant 800 and to fill the inflatable cuff.

The deployment of the implant 800 can be controlled by the PFL tubes 916 that are detachably coupled to the implant 800. The PFL tubes 916 are attached to the cuff 802 of the implant 800 so that the implant 800 can be controlled and positioned after it is removed from the sheath or delivery catheter 900. Preferably, three PFL tubes 916 are used, which can provide precise control of the implant 800 PFL tubes 916 during deployment and positioning. The PFL tubes 916 can be used to move the implant 800 proximally and distally, or to tilt the implant 800 and change its angle relative to the native anatomy.

Figure 8C:
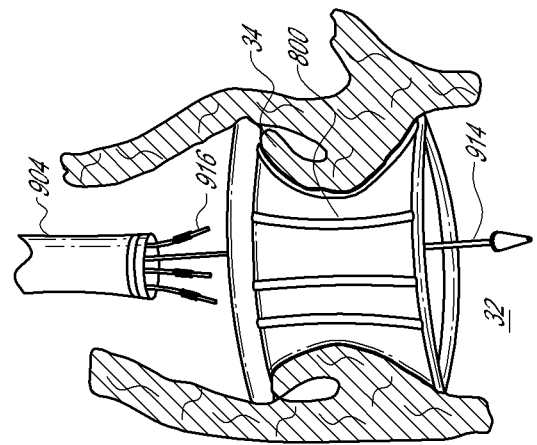
FIGS. 8A-C illustrate time sequence steps of partially deploying and positioning an artificial valve implant.
Figure 8B:
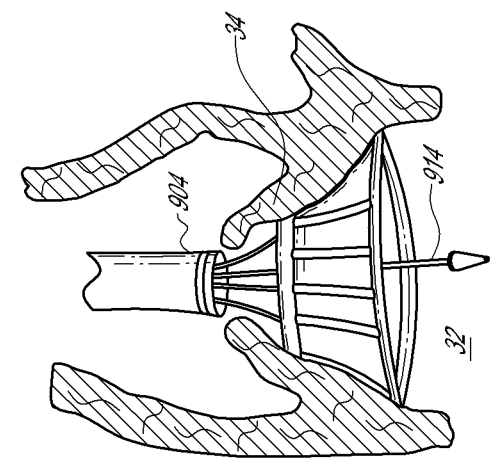
Figure 8A:
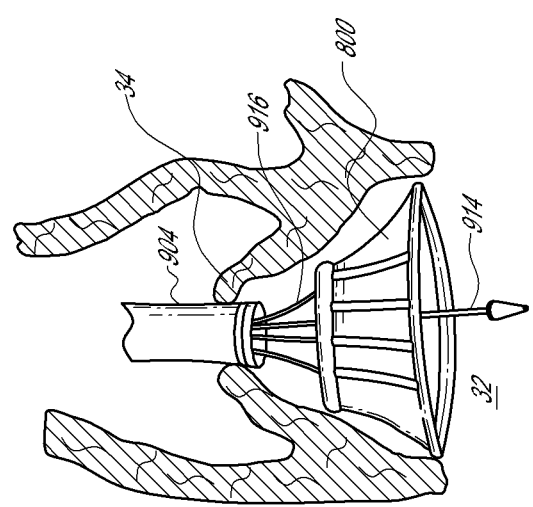

In some embodiments, the implant 800 contains multiple inflation valves 810 to allow the operator to inflate specific areas of the implant 800 with different amounts of a first fluid or a first gas. With reference to FIGS. 8A-C, in some embodiments, the implant 800 is initially deployed partially in the ventricle 32 (FIG. 8A). The inflation channel 808 is filled partially, allowing the distal portion of the implant 800 to open to approximately its full diameter. The implant is then pulled back into position at or near the native valve 34 annulus (FIG. 8B). In some embodiments, the distal toroid 807b is at least partially inflated first, and the cardiovascular prosthetic implant 800 is then retracted proximally for positioning the cuff across the native valve 34. The distal ring 807b seats on the ventricular side of the aortic annulus, and the implant 800 itself is placed just above the native valve 34 annulus in the aortic root. At this time, the PFL tubes 916 may act to help separate fused commissures by the same mechanism a cutting balloon can crack fibrous or calcified lesions. Additional inflation fluid or gas may be added to inflate the implant 800 fully, such that the implant 800 extends across the native valve annulus extending slightly to either side (See FIG. 8C). The PFL tubes 916 provide a mechanism for force transmission between the handle of the deployment catheter 900 and the implant 800. By moving all of the PFL tubes 916 together or the inner tubular member 904, the implant 800 can be advanced or retracted in a proximal or distal direction. By advancing only a portion of the PFL tubes 916 relative to the other PFL tubes 916, the angle or orientation of the implant 800 can be adjusted relative to the native anatomy. Radiopaque markers on the implant 800 or on the PFL tubes 916, or the radio-opacity of the PFL tubes 916 themselves, can help to indicate the orientation of the implant 800 as the operator positions and orients the implant 800.

In some embodiments, the implant 800 has two inflation valves 810 at each end of the inflation channel 808 and a check valve 811 in the inflation channel 808. The check valve 811 is positioned so the fluid or gas can flow in the direction from the proximal toroid 807a to the distal toroid 807b. In some embodiments, the implant 800 is fully inflated by pressurizing the endoflator attached to the first PFL tube 916 that is in communication with the first inflation valve 810 that leads to the proximal toroid 807a, while the endoflator attached to the second inflation valve 810 that is in communication with the distal toroid 807b is closed. The fluid or gas can flow into the distal toroid 807b through the one-way check valve. The proximal toroid 807a is then deflated by de-pressurizing the endoflator attached to the second inflation valve. The distal toroid 807b will remain inflated because the fluid or gas cannot escape through the check valve 811. The implant 800 can then be positioned across the native annulus. Once in the satisfactory placement, the proximal toroid 807a can then be inflated again.

In some embodiments, the implant 800 may only have one inflation valve. When the inflation channel 808 is inflated with the first fluid or gas, the proximal portion of the implant 800 may be slightly restricted by the spacing among the PFL tubes 916 while the distal portion expands more fully. In general, the amount that the PFL tubes 916 restricts the diameter of the proximal end of the implant 800 depends on the length of the PFL tubes 916 extend past the outer tubular member 901, which can be adjusted by the operator. In other embodiments, burst discs or flow restricters are used to control the inflation of the proximal portion of the implant 800.

Figure 9C:
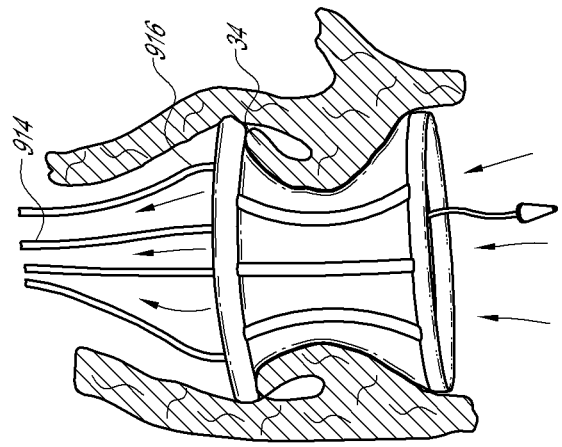
FIGS. 9A-E illustrates time sequence steps of deploying, testing and repositioning an artificial valve implant.
Figure 9B:
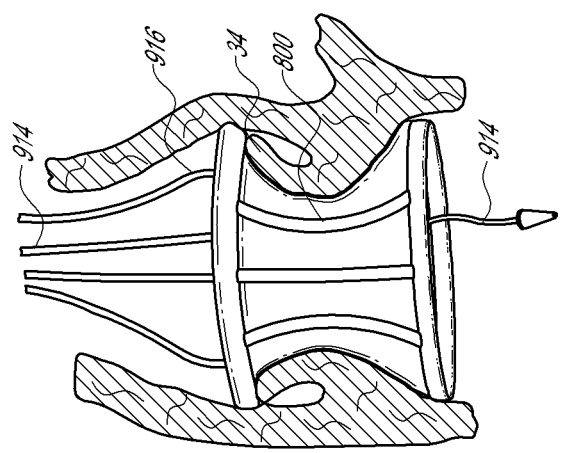
Figure 9A:
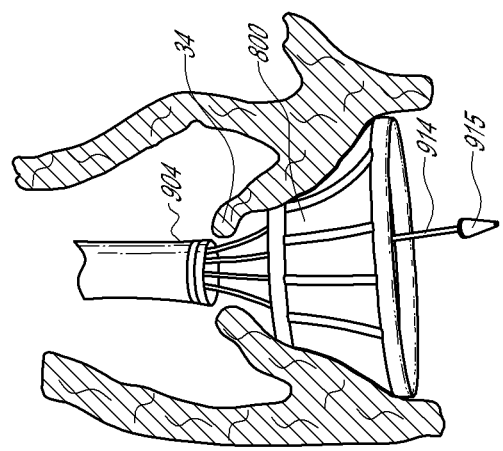
Figure 9E:
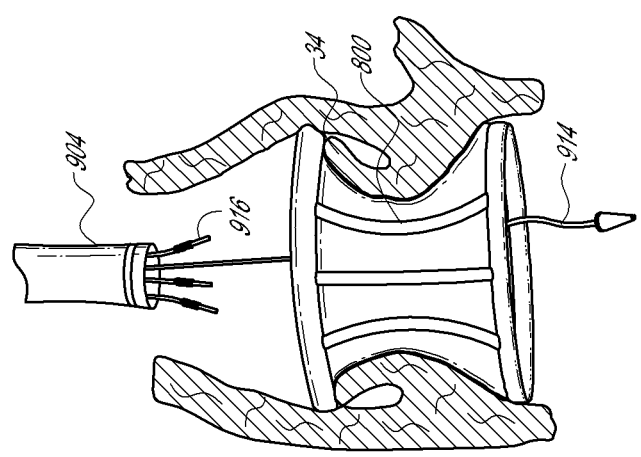
Figure 9D:
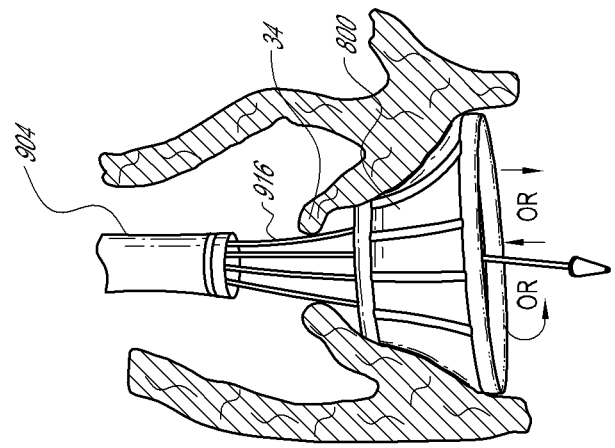

The implant 800 can also be deflated or partially deflated for further adjustment after the initial deployment. As shown in FIG. 9A, the implant 800 is partially deployed and the PFL tubes 916 used to seat the implant 800 against the native aortic valve 34. The implant 800 can then be fully deployed as in shown in FIG. 9B and then tested as shown in FIG. 9C. If justified by the test, the implant 800 can be deflated and moved as shown in FIG. 9D to a more optimum position. The implant 800 can then be fully deployed and released from the control wires as shown in FIG. 9E.

As discussed above, in some embodiments, the first inflation fluid or gas can be displaced by an inflation media that can harden to form a more permanent support structure in vivo. Once the operator is satisfied with the position of the implant 800, the PFL tubes 916 are then disconnected, and the catheter is withdrawn leaving the implant 800 behind (see FIG. 8C), along with the hardenable inflation media. The inflation media is allowed to solidify within the inflatable cuff. The disconnection method may included cutting the attachments, rotating screws, withdrawing or shearing pins, mechanically decoupling interlocked components, electrically separating a fuse joint, removing a trapped cylinder from a tube, fracturing a engineered zone, removing a colleting mechanism to expose a mechanical joint or many other techniques known in the industry. In modified embodiments, these steps may be reversed or their order modified if desired.

The above-describe method generally describes an embodiment for the replacement of the aortic valve. However, similar methods could be used to replace the pulmonary valve or the mitral or tricuspid valves. For example, the pulmonary valve could be accessed through the venous system, either through the femoral vein or the jugular vein. The mitral valve could be accessed through the venous system as described above and then trans-septaly accessing the left atrium from the right atrium. Alternatively, the mitral valve could be accessed through the arterial system as described for the aortic valve, additionally the catheter can be used to pass through the aortic valve and then back up to the mitral valve. Additional description of mitral valve and pulmonary valve replacement can be found in U.S. Patent Publication No. 2009/0088836 to Bishop et al.

Implant Recovery

Current valve systems are often deployed through a stent-based mechanism where the valve is sewn to the support structure. In the inflated embodiments described herein, the structure is added to the implant secondarily via the inflation fluid. This allows the user to inflate or pressurize the implant 800 with any number of media including one that will solidify. As such, if the operator desires, the implant 800 can be moved before the inflation media is solidified or depressurization can allow for movement of the implant within the body. Since catheter based devices tend to be small in diameter to reduce trauma to the vessel and allow for easer access to entry, it often difficult to remove devices such as stents once they have been exposed or introduced into the vasculature. However, as will be explained below, a device described herein enables a percutaneous prosthetic aortic valve to be recovered from the body and reintroduced retrograde to the introducer.

With reference to FIGS. 10A-C, the deployment control device also provides a method for retracting the implant 800 back into the introducer if the result is not satisfactory, or if the sizing of the implant could be optimized. Thus, after the implant 800 is fully or partially deployed (FIG. 10A), in addition to providing a mechanism to transmit axial force to the implant 800, the PFL tubes 916 described above provide a guide or ramp to pull the implant 800 back into the introducer as it is retracted as shown in FIGS. 10B and 10C. In some embodiments, the outer tubular member 901 is retracted out of the vessel while leaving the inner tubular member 904 still attached to the implant 800 prior to introducing the recovery catheter 930.

To recapture an inflatable implant 800, the implant is first deflated (FIG. 10B). In some embodiment, the implant 800 may be retracted to the tip of the inner tubular member 904 by pulling the PFL tubing 916 proximally, and the implant 800 and the delivery catheter 900 are then retracted to the tip of the introducer. The inner sheath handle 907 may be removed by unthreading the distal portion and sliding off at the proximal end of the delivery catheter 900. In some embodiments, the luer connections 917 on the proximal end of the PFL tubing 916 may be cut off for the removal of the inner sheath handle 907. Optionally a pushing tube can be loaded over the guidewire and PFL tubing until adjacent to the proximal end of the inner tubular member 904. The outer tubular member 901 can then be removed from the delivery catheter system, while keeping the implant 800 stationary.

The recovery catheter 930 can then be advanced over the guidewire and the inner tubular member 904. Once the recovery catheter 930 is proximate to the implant, the recovery sheath 931 is retracted to expose the basket section 933. The implant 800 can then be retracted into the basket section 933 (FIG. 10C). Once the implant 800 is completely inside the basket section 933, in some embodiments, the PFL tubes 916 are adjusted to offset the end valves 810 in the implant 800 to allow more compact fold. The recovery system 930 is then slowly pulled back through the introducer and out of the patient.

Figure 11:
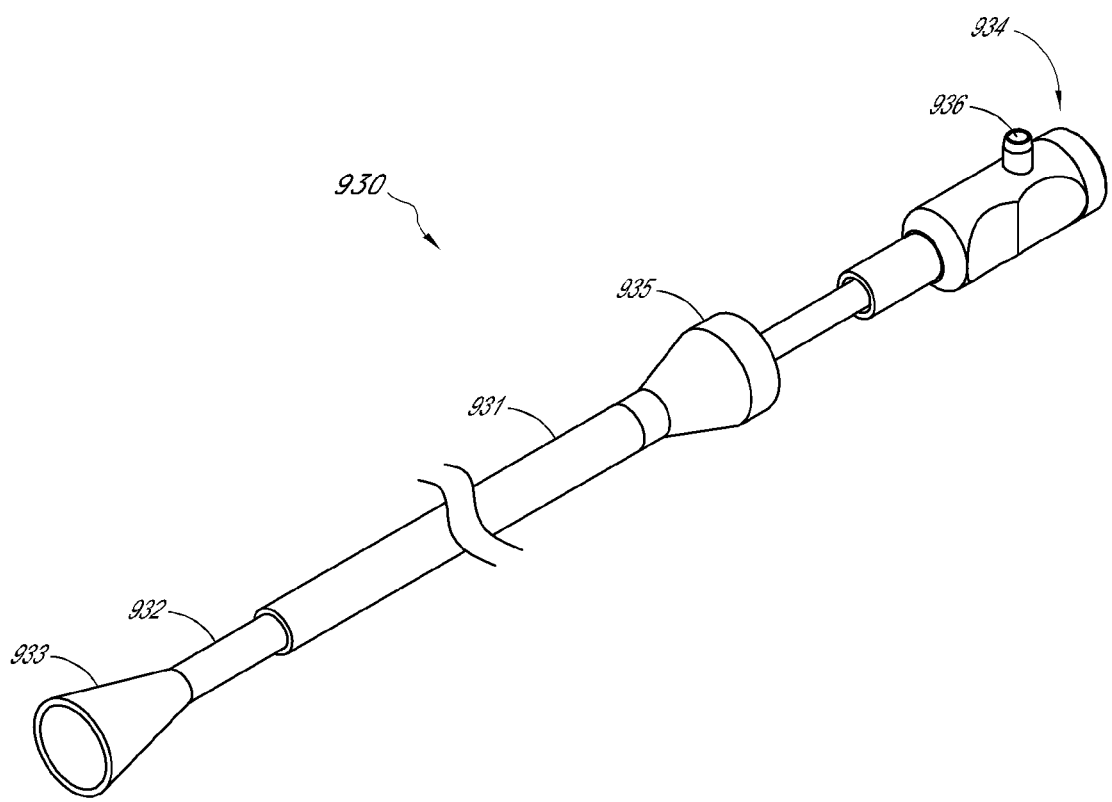
FIG. 11 is a side perspective view of an embodiment of recovery catheter for retrieving the implant in the patient.

FIG. 11 illustrates one embodiment of a recovery catheter 930 for recapturing an implant 800. As shown, the recovery catheter 930 comprises an outer recovery sheath 931. The outer recovery sheath 931 is inserted over the inner shaft 932. The inner shaft 932 comprises a basket structure 933, which is coupled to the distal end of the inner shaft 932 and is configured to capture the implant into the outer recovery sheath 931 without harm to the patient. Relative movement of the inner shaft 932 with respect to the outer recovery sheath 931 would expose the basket 933 when introduced into the body. By pulling the implant 800 into the basket section 933 it may be safely reintroduced into the introducer or outer recovery sheath 931. The basket 933 allows the implant to be guided into an introducer without harm or worry of the implant being tethered or compiled to a larger diameter where it may not fit into the inner diameter of a sheath.

The outer recovery sheath 931 is attached to the outer recovery handle or hub 935 at the proximal end, while the inner shaft 932 is attached to the inner recovery handle or hub 934 at the proximal end. A hemostasis valve (not shown) is preferably disposed in each of the inner and outer recovery handles 934 and 935. Also on the inner recovery handle 934, a flush port 936 and stop-cock can be provided for fluid introduction. In one embodiment, the inner shaft 932 would have a length of about 40 to 60 centimeters and a diameter of about 2 to about 10 millimeters. In a preferred embodiment, the outer diameter of the inner shaft 932 is less than or equal to 0.207". The basket section 933 may be constructed with materials such as polymeric strands or Nitinol, stainless steel or MP35N wire and attached by glue or thermal bonding techniques know in the industry. This wire, strand or ribbon may have a diameter or dimension of about 0.002 to 0.020 of an inch. The set or expanded shape would be about 1.00 to 1.50 inches and the length of the basket section 933 would measure about 6 to 9 inches in length. In another embodiment, the basket section 933 is made out of a fabric, where the fabric basket may contain a feature such as a preshaped wire or a balloon to facilitate its opening.

The basket section 933 can be formed by heat setting or other manners into a cone shape with a free diameter slightly larger than the patients aorta. In another embodiment, the braided basket is manufactured from loops of wire so that the cut ends of the wire are all located at the proximal end of the basket. The wires used to manufacture the basket 933 preferably have a diameter from 0.002 in to 0.020 in. The wires may also be replaced by ribbons having a thickness between 0.002 in and 0.020 in and a width between 0.003 in and 0.030 in. The diameter of the small end of the basket is preferably between 0.007 in and 0.3 in the basket is preferably be capable of collapsing to a diameter small enough to pass through the desired introducer size. The large end of the basket section preferably expands to a diameter similar to or slightly larger than the typical human aorta, or 0.75 in to 1.50 in.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A delivery catheter for deploying a cardiovascular prosthetic implant using a minimally invasive procedure, wherein the delivery catheter comprises:
    an elongate, flexible catheter body having a proximal end and a distal end, wherein the distal end has an outer diameter of 18 French or less;
    a cardiovascular prosthetic implant at the distal end of the catheter body, wherein the cardiovascular prosthetic implant comprises an inflatable cuff and a natural tissue valve comprising a leaflet having a thickness of at least about 0.011 inches coupled to the inflatable cuff; and
    at least one link between the catheter body and the cardiovascular prosthetic implant, wherein the tissue valve is loaded within the distal end.

2. The delivery catheter of claim 1, further comprising an outer tubular member in which the cardiovascular prosthetic implant is stored in a collapsed state for delivery.

3. The delivery catheter of claim 1, wherein the at least one link is a position-and-fill lumen configured for positioning the implant and for filling the inflatable cuff.

4. The delivery catheter of claim 1, wherein the inflatable cuff comprises at least one inflatable channel that forms, at least in part, a distal toroid, a proximal toroid and at least two struts between the distal toroid and the proximal toroid.

5. The delivery catheter of claim 4, wherein the struts are substantially perpendicular to the distal and the proximal toroids.

6. The delivery catheter of claim 4, wherein the cardiovascular prosthetic implant further comprises at least two inflation valves disposed in two end sections of the at least one inflatable channel.

7. The delivery catheter of claim 6, wherein each of the inflation valves comprises a sealing mechanism.

8. The delivery catheter of claim 6, further comprising a directional valve between the two end sections of the at least one inflation channel.

9. The delivery catheter of claim 6, wherein the cardiovascular prosthetic implant further comprises at least two links, and the at least two links are coupled to the at least two inflation valves.

10. The delivery catheter of claim 6, wherein the cardiovascular prosthetic implant further comprises a connection port coupled to a third link between the catheter body and the cardiovascular prosthetic implant.

11. The delivery catheter of claim 10, wherein the inflation valves and the connection port are staggered when the cardiovascular prosthetic implant is in a collapsed state.

12. The delivery catheter of claim 1, wherein the cardiovascular prosthetic implant has an outside diameter of greater than about 22 millimeters when fully inflated.

13. The delivery catheter of claim 12, wherein the tissue valve is attached to the cuff.

14. The delivery catheter of claim 12, wherein the tissue valve comprises three individual leaflets that are individually attached to the cuff.

15. A method of deploying a cardiovascular prosthetic implant, the method comprising the steps of:
    translumenally advancing a catheter of claim 1 to a position proximate a native valve of a patient;
    inflating the inflatable cuff fully with a hardenable inflation media; and removing the catheter from the patient, leaving the hardenable inflation media in the cardiovascular prosthetic implant within the patient.

16. The method of claim 15, further comprising inflating a distal toroid of the inflatable cuff with a first liquid and positioning the cardiovascular prosthetic implant using the at least one link before inflating the inflatable cuff fully with the hardenable media.

17. The method of claim 16, further comprising displacing the first liquid in the inflatable cuff with the hardenable inflation media.

18. The method of claim 16, wherein inflating the distal toroid and inflating the inflatable cuff are done using the at least one link.

19. The method of claim 16, further comprising allowing the inflation media to solidify within the inflatable cuff.

20. The method of claim 16, further comprising proximally retracting the cardiovascular prosthetic implant after the distal toroid is at least partially inflated.

21. A delivery catheter for deploying a cardiovascular prosthetic implant using a minimally invasive procedure, wherein the delivery catheter comprises:
   an elongate, flexible catheter body having a proximal end and a distal end, wherein the distal end has an outer diameter of 18 French or less; and
   a cardiovascular prosthetic implant loaded within the distal end of the catheter body, wherein the cardiovascular prosthetic implant comprises a support structure and a natural tissue valve comprising a leaflets having a thickness of at least about 0.011 inches coupled to the support structure.

22. A method of deploying a cardiovascular prosthetic implant, the method comprising the steps of:
   translumenally advancing a catheter of claim 21 to a position proximate a native valve of a patient; and
   deploying the cardiovascular prosthetic implant within the patient; and
   removing the catheter from the patient.

* * * * *

(12) INTER PARTES REVIEW CERTIFICATE (2992nd)
United States Patent      (10) Number:      US 9,603,708 K1
Robin et al.               (45) Certificate Issued:   Jan. 30, 2023

(54) LOW CROSSING PROFILE DELIVERY CATHETER FOR CARDIOVASCULAR PROSTHETIC IMPLANT

(75) Inventors: Kevin Robin; Do Uong; Gordon Bishop

(73) Assignee: SPEYSIDE MEDICAL LLC

Trial Number:

IPR2021-00244 filed Jan. 20, 2021

Inter Partes Review Certificate for:

Patent No.: 9,603,708
Issued:     Mar. 28, 2017
Appl. No.:  13/110,780
Filed:      May 18, 2011

The results of IPR2021-00244 are reflected in this inter partes review certificate under 35 U.S.C. 318(b).

INTER PARTES REVIEW CERTIFICATE
U.S. Patent 9,603,708 K1
Trial No. IPR2021-00244
Certificate Issued Jan. 30, 2023

AS A RESULT OF THE INTER PARTES REVIEW PROCEEDING, IT HAS BEEN DETERMINED THAT:

Claims 21 and 22 are cancelled.

\* \* \* \* \*